United States Patent
Qi et al.

(10) Patent No.: US 9,429,577 B2
(45) Date of Patent: Aug. 30, 2016

(54) ANTI-UROPLAKIN II ANTIBODIES SYSTEMS AND METHODS

(71) Applicant: Biocare Medical, LLC, Concord, CA (US)

(72) Inventors: Weimin Qi, Martinez, CA (US); David Tacha, San Ramon, CA (US)

(73) Assignee: Biocare Medical, LLC, Concord, CA (US)

( * ) Notice: Subject to any disclaimer, the term of this patent is extended or adjusted under 35 U.S.C. 154(b) by 0 days.

(21) Appl. No.: 14/432,132

(22) PCT Filed: Sep. 26, 2013

(86) PCT No.: PCT/US2013/062043
§ 371 (c)(1),
(2) Date: Mar. 27, 2015

(87) PCT Pub. No.: WO2014/052672
PCT Pub. Date: Apr. 3, 2014

(65) Prior Publication Data
US 2015/0247861 A1   Sep. 3, 2015

Related U.S. Application Data

(60) Provisional application No. 61/706,312, filed on Sep. 27, 2012.

(51) Int. Cl.
*C07K 16/28* (2006.01)
*C07K 16/30* (2006.01)
*G01N 33/574* (2006.01)
*G01N 33/53* (2006.01)

(52) U.S. Cl.
CPC ......... *G01N 33/57492* (2013.01); *C07K 16/28* (2013.01); *C07K 16/3038* (2013.01); *C07K 2317/34* (2013.01); *C07K 2317/56* (2013.01); *G01N 2333/705* (2013.01)

(58) Field of Classification Search
CPC  C07K 14/47; C07K 14/705; C07K 14/4727; C07K 16/28; C07K 2317/34; C07K 16/18; C07K 16/30; C07K 2317/26; C07K 2319/01; C07K 2319/10; C07K 14/65; C07K 16/1232
See application file for complete search history.

(56) References Cited

U.S. PATENT DOCUMENTS

| | | | |
|---|---|---|---|
| 4,145,406 A | 3/1979 | Schick et al. | |
| 4,254,082 A | 3/1981 | Schick et al. | |
| 4,687,732 A | 8/1987 | Ward et al. | |
| 4,690,890 A | 9/1987 | Loor et al. | |
| 4,792,521 A | 12/1988 | Shochat | |
| 4,863,875 A | 9/1989 | Bailey et al. | |
| 5,089,423 A | 2/1992 | Diamandis et al. | |
| 5,108,896 A | 4/1992 | Philo et al. | |
| 5,252,487 A | 10/1993 | Bacus et al. | |
| 5,482,698 A | 1/1996 | Griffiths | |
| 5,487,975 A | 1/1996 | Miller et al. | |
| 5,565,332 A | 10/1996 | Hoogenboom et al. | |
| 5,620,845 A | 4/1997 | Gould et al. | |
| 5,691,154 A | 11/1997 | Callstrom et al. | |
| 5,719,063 A | 2/1998 | Block | |
| 5,869,274 A | 2/1999 | Tsao et al. | |
| 5,891,658 A | 4/1999 | Klainer et al. | |
| 6,008,057 A | 12/1999 | Glass et al. | |
| 6,051,693 A | 4/2000 | Handley et al. | |
| 6,252,053 B1 | 6/2001 | Ohbayashi | |
| 6,403,769 B1 | 6/2002 | Larochelle et al. | |
| 6,409,990 B1 | 6/2002 | Vera | |
| 6,476,206 B1 | 11/2002 | Sidransky et al. | |
| 6,537,745 B2 | 3/2003 | Chien et al. | |
| 6,580,056 B1 | 6/2003 | Tacha | |
| 6,723,506 B2 | 4/2004 | Fletcher et al. | |
| 6,946,256 B1 | 9/2005 | McKeon et al. | |
| 7,422,739 B2 | 9/2008 | Anderson et al. | |
| 7,468,425 B2 | 12/2008 | Sidransky et al. | |
| 7,674,605 B2 | 3/2010 | Lin et al. | |
| 7,785,803 B2 | 8/2010 | Achen et al. | |
| 7,846,726 B2 | 12/2010 | Li et al. | |
| 7,846,762 B2 | 12/2010 | Rana et al. | |
| 7,875,705 B2 | 1/2011 | Iwaneri et al. | |
| 7,935,794 B2 | 5/2011 | Pullen | |
| 7,935,795 B2 | 5/2011 | Nakajima | |
| 7,935,796 B2 | 5/2011 | Lee et al. | |
| 7,973,138 B2 | 7/2011 | Liang et al. | |
| 8,153,126 B2 | 4/2012 | Violette et al. | |
| 8,168,409 B2 | 5/2012 | Calzone et al. | |
| 8,338,576 B2 | 12/2012 | Paralkar et al. | |

(Continued)

FOREIGN PATENT DOCUMENTS

| EP | 2402370 A1 | 1/2012 |
|---|---|---|
| EP | 1733437 B1 | 9/2014 |

(Continued)

OTHER PUBLICATIONS

Brown, H. M. et al. Uroplakin-III to Distinguish Primary Vulvar Paget Disease From Paget Disease Secondary to Urothelial Carcinoma, Human Path. 2002;33:545-548.
Koga, F. et al. Impaired p63 Expression Associates with Poor Prognosis and Uroplakin III Expression in Invasive Urothelial Carcinoma of the Bladder, Clin Cancer Res. 2003;9:5501-5507.
Logani, S. et al. Immunoprofile of Ovarian Tumors With Putative Transitional Cell (Urothelial) Differentiation Using Novel Urothelial MarkersHistogenetic and Diagnostic Implications, Am J Surg Pathol 2003;27:1434-1441.
Matsumoto, K. et al. Loss Expression of Uroplakin III is Associated with Clinicopathologic Features of Aggressive Bladder Cancer, Urology. 2008;72:444-449.
Mhawech, P. et al. Immunohistochennical Profile of High-Grade Urothelial Bladder Carcinoma and Prostate Adenocarcinoma, Human Path. 2002;33:1136-1140.

(Continued)

*Primary Examiner* — Shafiqul Haq
*Assistant Examiner* — Carmencita M Belei
(74) *Attorney, Agent, or Firm* — Santangelo Law Offices, P.C.

(57) ABSTRACT

The present invention is related to the anti-Uroplakin II antibodies, kits, cocktails, and use of anti-Uroplakin II antibodies for detection of cancer.

12 Claims, 28 Drawing Sheets

(56) References Cited

U.S. PATENT DOCUMENTS

| | | |
|---|---|---|
| 8,603,765 B2 | 12/2013 | Tacha |
| 8,852,592 B2 | 10/2014 | Qi et al. |
| 9,005,612 B2 | 4/2015 | Ledbetter et al. |
| 9,156,915 B2 | 10/2015 | Waldman et al. |
| 2002/0106685 A1 | 8/2002 | Henning et al. |
| 2002/0173053 A1 | 11/2002 | Damaj et al. |
| 2003/0017491 A1 | 1/2003 | Shi et al. |
| 2005/0186642 A1 | 8/2005 | Tacha |
| 2006/0148063 A1 | 7/2006 | Fauzzi et al. |
| 2007/0015908 A1 | 1/2007 | Fischer et al. |
| 2007/0041972 A1 | 2/2007 | Rother et al. |
| 2009/0191190 A1 | 7/2009 | Barghorn et al. |
| 2010/0004782 A1 | 1/2010 | Tacha |
| 2010/0047825 A1 | 2/2010 | Tacha |
| 2010/0092457 A1 | 4/2010 | Aburatani et al. |
| 2012/0082999 A1 | 4/2012 | Liao et al. |
| 2012/0245051 A1 | 9/2012 | Rimm et al. |
| 2012/0321557 A1 | 12/2012 | Kimura |
| 2014/0004542 A1 | 1/2014 | Qi et al. |
| 2014/0057803 A1 | 2/2014 | Tacha |
| 2015/0056635 A1 | 2/2015 | Qi et al. |
| 2015/0152180 A1 | 6/2015 | Davis et al. |
| 2016/0009795 A1 | 1/2016 | Tacha et al. |

FOREIGN PATENT DOCUMENTS

| | | |
|---|---|---|
| WO | 03/003906 A2 | 1/2003 |
| WO | 2005054860 A1 | 6/2005 |
| WO | 2005076005 A2 | 8/2005 |
| WO | 2005083802 A1 | 9/2005 |
| WO | 2010/022736 A2 | 3/2010 |
| WO | 2010/124689 A1 | 11/2010 |
| WO | 2012/031273 A2 | 3/2012 |
| WO | 2012/154983 A2 | 11/2012 |
| WO | 2012154983 A2 | 11/2012 |
| WO | 2014/052672 A1 | 4/2014 |
| WO | 2014100220 A2 | 6/2014 |
| WO | 2014134587 A1 | 9/2014 |
| WO | 2015051320 A2 | 4/2015 |

OTHER PUBLICATIONS

Ogawa, K. et al. Immunohistochemical Analysis of Uroplakins, Urothelial Specific Proteins, in Ovarian Brenner Tumors, Normal Tissues, and Benign and Neoplastic Lesions of the Female Genital Tract, Am J Pathol. 1999;155:1047-1050.

Ohtsuka, Y. et al. Loss of uroplakin III expression is associated with a poor prognosis in patients with urothelial carcinoma of the upper urinary tract, BJU International, 2006;97:1322-1326.

Budapest restricted certificate of deposit Budapest treaty on the international recognition of the depoit of microorganisms for the purposes of patent procedure international form Receipt in the case of an original deposit issued pursuant to rule 7.3 and viability statement issued pursuant to rle 10.2, Anti-human UPII mouse hybridoma: BC21, PTA-13181, 25 vials, Deposited on Behalf of: Biocare Medical, Inc., Date of Receipt of seeds/strains(s) by the ATCC: Sep. 6, 2012.

Wu, RL et al. Uroplakin II Gene is Expressed in Transitional Cell Carcinoma But Not in Biharzial Bladder Squamous Cell Carcinoma: Alternative Pathways of Bladder Epithelial Differentiation and Tumor Formation. Cancer Research, Mar. 15, 1998, vol. 58, No. 6: 1291-1297.

U.S. Appl. No. 61/706,312, filed Sep. 27, 2012; entitled Systems and Methods for Anti-Uroplakin II Antibodies.

U.S. Appl. No. 13/830,473, filed Mar. 14, 2013; entitled Systems and Methods for Anti-Uroplakin III Antibodies, entire image wrapper available on USPTO Pair.

Kaufmann, O. et al. Uroplakin III is a Highly Specific and Moderately Sensitive Immunohistochemical Marker for Primary and Metastatic Urothelial Carcinomas, Am J Clin Pathol 2000;113:683-687.

Wu XR, Kong XP, Pellicer A, Kreibich G, Sun TT.; Uroplakins in urothelial biology, function, and disease; Kidney Int. Jun. 2009;75(11):1153-65.

Wu X, Kakehi Y, Zeng Y, Taoka R, Tsunemori H, Inui M. J; Uroplakin II as a promising marker for molecular diagnosis of nodal metastases from bladder cancer: comparison with cytokeratin 20.; Urol. Dec. 2005;174(6):2138-42.

Olsburgh J, Harnden P, Weeks R, Smith B, Joyce A, Hall G, Poulsom R, Selby P, Southgate J.J; Uroplakin gene expression in normal human tissues and locally advanced bladder cancer Pathol. Jan. 2003;199(1):41-9.

Lu JJ, Kakehi Y, Takahashi T, Wu XX, Yuasa T, Yoshiki T, Okada Y, Terachi T, Ogawa O; Detection of circulating cancer cells by reverse transcription-polymerase chain reaction for uroplakin II in peripheral blood of patients with urothelial cancer; Clin Cancer Res. Aug. 2000;6(8):3166-71.

Li SM, Zhang ZT, Chan S, McLenan O, Dixon C, Taneja S, Lepor H, Sun TT, Wu XR; Detection of circulating uroplakin-positive cells in patients with transitional cell carcinoma of the bladder; J Urol. Sep. 1999;162(3 Pt 1):931-5.

Kong XT, Deng FM, Hu P, Liang FX, Zhou G, Auerbach AB, Genieser N, Nelson PK, Robbins ES, Shapiro E, Kachar B, Sun TT.; Roles of uroplakins in plaque formation, umbrella cell enlargement, and urinary tract diseases. J Cell Biol. Dec. 20, 2004;167(6):1195-204.

Okegawa T, Kinjo M, Nutahara K, Higashihara E.; Value of reverse transcription polymerase chain assay in peripheral blood of patients with urothelial cancer. J Urol. Apr. 2004;171(4):1461-6.

Hong-Ying Huang, Shahrokh F. Shariat, Tung-Tien Sun, Herbert Lepor, Ellen Shapiro, Jer-Tsong Hsieh, Raheela Ashfaq, Yair Lotan, and Xue-Ru Wu, ; Persistent Uroplakin Expression in Advanced Urothelial Carcinomas: Implications in Urothelial Tumor Progression and Clinical Outcome. Hum Pathol. Nov. 2007; 38(11): 1703-1713.

International Application No. PCT/US13/62043, entitled Anti-Uroplakin II Antibodies Systems and Methods, filed Sep. 26, 2013.

International Application No. PCT/US13/62043, entitled Anti-Uroplakin II Antibodies Systems and Methods, filed Sep. 26, 2013, Search Report, dated Jan. 29, 2014. 6 pages.

International Application No. PCT/US13/62043, entitled Anti-Uroplakin II Antibodies Systems and Methods, filed Sep. 26, 2013, Written Opinion, dated Jan. 29, 2014. 22 pages.

Yu, C et al. PSA and NIKX3.1: A Comparative IHC Study of Sensitive and Specificity in Prostate Cancer. BioCareMedical, Presented at USCAP, Abstract #1070, Mar. 19-21, 2012. <uri: http://biocare.net/wp-content/uploads/PSANKX100.pdf>.

Chames et al. Therapeutic antibodies: success, limitations and hopes for the future. Themed Section: Vector Design and Drug Delivery Review. British Journal of Pharmacology (2009) 157, 200-233.

Jakobovits, Aya. Production of fully human antibodies by transgenic mice. Cell Genesys Inc., Foster City, USA. Current Opinion in Biotechnology 1995, 6:561-566.

Kellermann & Green, Antibody discovery: the use of transgenic mice to generate human monoclonal antibodies for therapeutics. Current Opinion in Biotechnology 2002, 13:593-597.

Morrison et al. Chimeric human antibody molecules: Mouse antigen-binding domains with human constant region domains. Proc. Natl. Adad. Sci. USA. vol. 81, pp. 6851-6855, Nov. 1984.

Winter et al. Humanized antibodies. Immunology Today vol. 14 No. 6 1993. 4 pages.

U.S. Appl. No. 15/026,904, filed Apr. 1, 2016. First Inventor: David Tacha.

Tacha et al. 'A 6-Anitbody Panel for the Classification of Lung Adenocarcinoma Versus Squamous Cell Carcinoma.' Appl Immunohistochem Mol Morphol. 20(3): 201-7, May 2012.

Baty et al. 'Gene profiling of Icinical routine biopsies and prefiction of survival in non-small cell lung cancer.' Am J Respir Crit Care Med. 181(2):181-8.15 Oct. 2009.

Brown, et al. 'Tissue Preserving Antibody Cocktails to Differentiate Primary Squamous Cell Carcinoma, Adenocarcinoma, and Small Cell Carcinoma of Lung.' Arch Pathol Lab Med. 137(9):1274-81. Jan. 4, 2013.

(56) References Cited

OTHER PUBLICATIONS

Whithaus K., et al. Evaluation of Napsin A, Cytokeratin 5/6, p63, and Thyroid Transcription Factor 1 in Adenocarcioma Versus Squamous Cell Carcinoma of Lung. Arch Pathol Lab Med. 2012; 136: 155-162.
Savci-Heijink C. D., et al. The role of desmoglein-3 in the diagnosis of squamous cell carcinoma of the lung. Am J Pathol. 2009;174(5): 1629-1637.
Ring B. Z., et al. A novel five-antibody immunohisto-chemical test for subclassification of lung carcinoma. Mod Pathol. 2009;22(8): 1032-1043.
Mukhopadhyay S., et al. Subclassification of Non-small Cell Lung Carcinomas lacking Morphologic Differentiation on biopsy specimens: Utility of an Immunohistochemical Panel Containing TTF-1, Napsin A, p63 and CK 5/6. Am J Surg Pathol, 2011; 35(1): 15-25.
Bishop J. A., p40 (ΔNp63) is superior to p63 for the diagnosis of pulmonary squamous cell carcinoma, Modern Pathology (2011), 1-11; republished Mar. 2012;25(3):405-15.
Ikeda S, et al. "Combined immunohistochemistry of beta-catenin, cytokeratin 7, and cytokeratin 20 is useful in discriminating primary lung adenocarcinomas from metastatic colorectal cancer.", BMC Cancer. Feb. 2, 2006;6:31.
Chopra, N. et al. 'Inducing Protectice Antibodies Against Ring-Infected Erythrocyte Surface Peptide Antigen of Plasmodium Falciparum Using Immunostimulating Complex (Iscoms) Delivery.' Med Microbiol. Immunol. Nov. 2000 vol. 189, No. 2: pp. 75-83.
Calbiochem-Novabiochem International. P40(Ab-1) Cat# PC373 [datasheet]. USA 2000; 2 pages.
Abcam. Understanding Secondary Antibodies: Fragment Antigen Binding Antibodies and Isotopes. USA 2012; 12 pages.
Biocare Medical. MACH 2 Double-Stain 2 [datasheet]. USA Mar. 2, 2011; 2 pages.
Yamaguchi, K. et al. Circulating Antibodies to P40AIS in the Sera of Respiratory Tract Cancer Patients. Int. J. Cancer. Nov. 20, 2000. vol. 89 No. 6; 5 pages.
Vaidyanathan, P. Aperio—Definins Digital Pathology Solutions [Presentation]. Jul. 7, 2011. Aperio Webinar. <http://www.aperio.com/sites/default/files/events/070611_Spectrum_Plus_ppt_for_webinar_on_integration.pd>; 10 pages.
Jain, et al. Atypical ductal hyperplasia: interobserver and intraobserver variability. Mod. Pathol. (2011) 24, 917-923.
Tacha, et al. "An Immunohitochemical Analysis of a Newly Developed Mouse Monocloncal p40 (BC28) in Lung, Bladder, Skin, Breast, Prostate, and Head and Neck Cancers" 2014 College of American Pathologists, Early Online Release, Arch Pathol. Lab Med. 8 pages, postes Feb. 2014.
Barbareschi, et al. p63, a p53 homologue, is a selective nuclear marker of myoepithelial cells of the human breast. Am J Surg. Pathol 25(8): 1054-1060,Aug. 2001.
Bergholz, et al. 'Role of p63 in development, tumorigenesis and cancer progression'. Cancer Microenvironment (2012) 5:311-322.
Di Como, et al. 'p63 Expression Profiles in Human Normal and Tumor Tissues'. Clinical Cancer Research. vol. 8, 494-501, Feb. 2002.
Hibi, et al. 'AIS is an oncogene amplified in squamous cell carcinoma'. Pro Natl Acad Sci U.S.A, May 9, 2000, vol. 97, No. 10, 5462-5467.
Kaghdad, et al. Monoallelically Expressed Gene Related to p53 a 1p36, a Region Frequently Deleted in Neuroblastoma and Other Human Cancers. Cell, vol. 90(4), 809-819, Aug. 22, 1997.
Karni-Schmidt, et al. Distinct Expression Profiles of p63 Variants during Urothelial Development and Bladder Cancer Progression. Am J Pathol vol. 178, No. 3, Mar. 2011, 1350-60.
Khoury, et al. "p53 Isoforms: An Intracellular Microprocessor?" Genes & Cancer, 2(4), 2011, 453-465.
Murray-Zmijewski, et al. p53/p63/p73 isoforms: an orchestra of isoforms to harmonise cell differentiation and response to stress. Cell Death and Differentiation (Jun. 2006); 13(6), 962-972.

Nobre, et al. 'p40: A p63 isoform useful for lung cancer diagnosis—a Review of the Physiological and Pathological Role of p63'. Acta Cytologica 2012; 57(1):1-8.
Nonaka, 'A study of Np63 expression in lung non-small cell carcinomas'. Am J Surg Pathol vol. 36 No. 6 Jun. 2012 895-9.
Nylander, et al. 'Differential expression of p63 isoforms in normal tissues and neoplastic cells'. J Pathol 2002; 198: 417-427.
Osada, et al. Cloning and functional analysis of human p51, which structurally and functinoally resembles p53, Nat Med. Jul. 1998; 4(7): 839-43.
Pelosi, et al. 'Np63 (p40) and Thyroid Transcription Factor-1 Immunoreactivity on small biopsies or cellblocks for typing non-small cell lung cancer'. Journal and Thoracic Oncology, vol. 7(2), No. 2, Feb. 2012, 281-90.
Senoo et al. 'A second p53-Related Protein, p73L, with High Homology to p73'. Biophys Res Commun. Jul. 30, 1998;248(3), 603-607.
Trink, et al. A new human p53 homologue, Nat Med. Jul. 1998; 4(7): 747-8.
Yang, et al. 'p63, a p53 homolog at 3q27-29, encodes multiple products with transactivating, death-inducing, and dominant-negative activities'. Molecular Cell, vol. 2(3), 305-316, Sep. 1998.
Bowen, et al. 'Emerging roles for PAX8 in ovarian cancer and endosalpingeal development.' Gynecologic Oncology, vol. 104, No. 2, Feb. 2007, 331-337.
Tacha, D. et al. Expression of PAX8 in Normal and Neoplastic Tissues: A Comprehensive Immunohistochemical Study. Appl. Immun. Mol. Morph. 2011.
Kobel M. et al. Ovarian carcinoma subtypes are different diseases: Implications for biomarker studies. PLoS Med. Dec. 2, 2008; 5(12): e232.
Nonaka D. et al. Expression of PAX8 as useful marker in distinguishing ovarian carcinomas from mammary carcinomas. Am J Surg Pathol. Oct. 2008; 32(10):1566-71.
Tong G. X. et al. Expression of PAX8 in nephrogenic adenoma and clear cell adenocarcinoma of the lower urinary tract: evidence of related histogenesis? Am J Surg Pathol. Sep. 2008; 32(9):1380-7.
Tong G. X. et al. Expression of PAX8 in normal and neoplastic renal tissues: an immunohistochemical study. Mod. Pathol. Sep. 2009; 22 (9):1218-27.
Mazal P. R. et al. Expression of aquaporins and Pax-2 compared to CD10 and cytokeratin 7 in renal neoplasms: a tissue microarray study. Mod. Pathol. Apr. 2005; 18(4):535-40.
Avery A. K. et al. Use of antibodies to RCC and CD10 in the differential diagnosis of renal neoplasms. Am J Surg Pathol. Feb. 2000; 24(2):203-10.
Zhou M. et al. The usefulness of immunohistochemical markers in the differential diagnosis of renal neoplasms. Clin Lab Med. Jun. 2005; 25(2):247-257.
Kuehn A. et al. Expression analysis of kidney-specific cadherin in a wide spectrum of traditional and newly recognized renal epithelial neoplasms: diagnostic and histogenetic implications. Am J Surg Pathol. Oct. 2007; 31(10):1528-33.
Mazal P. R. et al. Expression of kidney-specific cadherin distinguishes chromophobe renal cell carcinoma from renal oncocytoma. Hum Pathol. Jan. 2005; 36(1):22-8.
Zhu W. et al. WT1, monoclonal CEA, TTF1, and CA125 antibodies in the differential diagnosis of lung, breast, and ovarian adenocarcinomas in serous effusions. Diag Cytopathol. Jun. 2007; 35(6):370-5.
Tornos C. et al. Expression of WT1, CA 125, and GCDFP-15 as useful markers in the differential diagnosis of primary ovarian carcinomas versus metastatic breast cancer to the ovary. Am J Surg Pathol. Nov. 2005; 29(11):1482-9.
Lee A. H. et al. The expression of Wilms' tumour-1 and CA125 in invasive micropapillary carcinoma of the breast. Histopathology. Dec. 2007; 51(6):824-8.
Reid-Nicholson M. et al. Immunophenotypic diversity of endometrial adenocarcinomas: implications for differential diagnosis. Mod Pathol. Aug. 2006; 19(8):1091-100.
Zhang P. et al. Immunohistochemical analysis of thyroid-specific transcription factors in thyroid tumors. Pathol Int 2006;56:240-245.

(56) References Cited

OTHER PUBLICATIONS

Ozcan A. et al. PAX 8 expression in non-neoplastic tissues, primary tumors, and metastatic tumors: a comprehensive immunohistochemical study. Mod Pathol 2011;24:751-764.

Laury A.R. et al. A comprehensive analysis of PAX8 expression in human epithelial tumors. Am J Surg Pathol 2011;35:816-826.

Moretti L. et al. N-terminal PAX8 polyclonal antibody shows cross-reactivity with N-terminal region of PAX5 and is responsible for reports of PAX8 positivity in malignant lymphomas. Mod Pathol 2011.

Long K. B. et al. PAX8 Expression in well-differentiated pancreatic endocrine tumors: correlation with clinicopathologic features and comparison with gastrointestinal and pulmonary carcinoid tumors. Am J Surg Pathol 2010;34:723-729.

Haynes C. M. et al. PAX8 is expressed in pancreatic well-differentiated neuroendocrine tumors and in extrapancreatic poorly differentiated neuroendocrine carcinomas in fine-needle aspiration biopsy specimens. Cancer Cytopathol 2011;119:193-201.

Sangoi A. R. et al. PAX8 expression reliably distinguishes pancreatic well-differentiated neuroendocrine tumors from ileal and pulmonary well-differentiated neuroendocrine tumors and pancreatic acinar cell carcinoma. Mod Pathol 2011;24:412-424.

Lorenzo P.I. et al. Immunohistochemical assessment of Pax8 expression during pancreatic islet development and in human neuroendocrine tumors. Histochem Cell Biol 2011;136:595-607.

Ye J. et al. Diagnostic utility of PAX8, TTF-1 and napsin A for discriminating metastatic carcinoma from primary adenocarcinoma of the lung. Biotech Histochem 2011.

Albadine R. et al. PAX8 (+)/p63 (−) immunostaining pattern in renal collecting duct carcinoma (CDC): a useful immunoprofile in the differential diagnosis of CDC versus urothelial carcinoma of upper urinary tract. Am J Surg Pathol 2010;34:965-969.

Laury A.R. et al. PAX8 reliably distinguishes ovarian serous tumors from malignant mesothelioma. Am J Surg Pathol 2010;34:627-635.

Turque N. et al. Pax-QNR/Pax-6, a paired box-and homeobox-containing gene expressed in neurons, is also expressed in pancreatic endocrine cells. Mol Endocrinol 1994;8:929-938.

Tockman et al, Consideration in Bringing a Cancer Biomarker to Clinical Application. Cancer Research vol. 52 p. 2711s (1992).

Janicke et al., Urokinase-type Plasminogen Activator (u-PA) Antigen in a Predictor of Early Relapse in Breast Cancer. Fibrinolysis vol. 4 p. 69 (1990).

Paul, Structure and Function of Immunoglobulins. Fundemental Immunology, 3rd Edition, 1993, pp. 292-295.

Rudikoff et al Single Amino Acid Substitution Altering Antigen-binding Specificity (Proc. Natl. Acad. Sci. USA 1982 vol. 79: p. 1979-82).

de Pascalis et al., Grafting of "Abbreviated" Complementarity-Determining Regions Containing Specificity-Determining Residues Essential for Ligand Contact to Engineer a Less Immunogenic Humanized Monoclonal Anitbody. (The Journal of Immunology (2002) 169,3076-3084).

Brown et al. Tolerance to Single, but Not Multiple, Amino Acid Replacements in Anitbody VH CDR2. (J. Immunol. May 1996; 156(9):3285-3291.

Casset et al. A Peptide Mimetic of an Anti-CD4 Monoclonal Antibody by Rational Design. (2003) BBRC 307, 198-205.

Parker, D. C. et. al. Potential Utility of Uroplakin III, Thrombomodulin, High Molecular Weight Cytokeratin, and Cytokeratin 20 in Noninvasive, Invasive, and Metastatic Urothelial (Transitional Cell) Carcinomas, Am J Surg Pathol 2003;27:1-10.

Wu, X. R. et. al. Mammalian Uroplakins, A group of highly conserved urothelial differentiation-related membrane proteins, J Biol Chem. 1994;269:13716-13724.

Moll, R. et al. Uroplakins, Specific Membrane Proteins of Urothelial Umbrella Cells, as Histological Markers of Metastatic Transitional Call Carcinomas. Am J Pathol, vol. 147, No. 5, Nov. 1995.

Lai, Y. et al. UPK3A: A promising novel urinary marker for the detection of bladder cancer, Urology 76(2), 2010.

Saeb, Parsy, et al. 'Diagnosis of Bladder Cancer by Immunocytochemical detection of minichromosome maintenance protein-2 in cells retrieved from urine' British Journal of Cancer (2012) 107, 1384-1391.

Nonaka, D. et al. Diagnostic Utility of Thyroid Transcription factors PAX8 and TTF-2 in Thyroid Epithelial Neoplasms. Mod Pathol. Feb. 2008; 21(2): 192-2004.

Panka et al. Variable region framework differences result in decreased or increased affinity of variant anti-digoxin antibodies. Proc. Natl. Acad. Sci. USA, vol. 85, pp. 3080-3084, May 1988.

Harris et al. Assessing Genetic Heterogeneity in Production Cell Lines: Detection by Peptide Mapping of a Low Tyr to Gln Sequence Variant in a Recombinant Antibody. Biotechnology, vol. 11 p. 1293-1297, Nov. 1993.

Okazaki et al. Hydronephrosis associated with antiurothelial and antinuclear autoantibodies in BALB/ c-Fcgr2b-/-Pdcd1-/-mice. The Journal of Experimental Medicine. vol. 202, No. 12, pp. 1643-1648, Dec. 19, 2005.

Bondurand, et al. The role of SOX10 during enteric nervous system development. Dev Bioi. Epub May 2, 2013, 382 (1):330-43.

GenBank Accession No. CAG30470. SOX10 (*Homo sapiens*]. Oct. 16, 2008. (Retrieved from the Internet Dec. 4, 2014: <http://www.ncbi.nlm.nih.gov/protein/CAG30470.1>] 2 pages.

Sanderson, SO et. al., "An Analysis of the p63/αMethylacyl Coenzyme A Racemase Immunohistochemical Cocktail Stain in Prostrate Needs Biopsy Speciments and Tissue Microarrays", Am. J. Clin. Path., 2004; 121:220-225.

Zhou, Ming. al., "Basal Cell Cocktail (34βE12+p63) Improves the Detection of Prostate Basal Cells", Am. J. Surg. Path., 2003: 27(3), 365-371.

Zhou, Ming et al., "Expression and Disgnostic Utility of Alpha-Methylacyl-CoA-Racemase (P504S) in Foamy Gland and Pseudohyperplastic Prostate Cancer", Am. J. Surgical Pathology 27(6): 772-778, 2003.

Anonymous: "PIN cocktail-2 (P504S+p63)", Biocarta. May 4, 2003, pp. 1-2. XP 002667408, Retrieved from the Internet: URL:http://www.biocarta.com/TDS/PM205DSH.pdf [retrieved on Jan. 18, 2012].

Anonymous: "Double vision. The double stain, polymer detection system", Biocare Medical, Aug. 2, 2003, pp. 1-3, XP002667409, retrieved from the Internet: URL: htt12 ://web/archive. org/web/20030802112943/httQ :1/biocare. net/Detection. htm [retrieved Jan. 18, 2012].

Anonymous: "Double vision, The double stain, polymer detection system", Biocare Medical, Oct. 2, 2003, pp. 1-3, XP002667410, retrieved from the Internet: URL:htt12 ://web/archive .org/web/20031 002060452/httQ ://biocare. net/Detection. htm[retrieved Jan. 18, 2012).

Anonymous: "Double vision, The double stain, polymer detection system", Biocare Medical, Jan. 1, 2004, pp. 1-5, XP002667411, retrieved from the Internet: URL: htt12 ://web/archive .org/web/20040 1 01180833/httQ :1/biocare. net/Detection. htm [retrieved Jan. 18, 2012].

Susan Van Noorden., "Immunocytochemistry for light microscopy a technical update", The biomedical Scientist, XP-002522654, Aug. 2003, pp. 808-811.

Rami Suzuki. et al., "Proliferation and differentiation in the human breast during pregnancy", Differentiation. vol. 66, No. 2-3, XP-002522647, Oct. 2000, pp. 106-115.

BioGenex datasheet, Rabbit Anti-PIN4 Cocktail-AB448ME, Doc. No. 932—448ME Rev A, release date Aug. 17, 2007.

van der Loos, "Immunoenzyme Multiple Staining Methods", Microscopy Handbooks 45, (1999); Bios Scientific Publishers Ltd: Oxford, UK.

Hiromichi Tsurui, et al., "Seven-color Fluorescence Imaging of Tissue Samples Based on Fourier Spectroscopy and Singular Value Decomposition", The Journal of Histochemistry & Cytochemistry, vol. 48, No. 5, XP-002522648, May 2000, pp. 653-662.

David Y. Mason, et al., "Double immunofluorescence labelling of routinely processed paraffin sections", Journal of Pathology, vol. 191, No. 4. XP-002522649, Aug. 2000, pp. 452-461.

(56) References Cited

OTHER PUBLICATIONS

Susan Van Noorden., "Advances in immunocytochemistry", Folia Histochemica et Cytobiologica, vol. 40, No. 2, XP-008104795, 2002, pp. 121-124.
Van der Loos, et al., "Immunohistochemical Detection of Interferon-y: Fake or Fact?", The Journal of Histochemistry & Cytochemistry, vol. 49, No. 6, XP-002522653, Jun. 2001. pp. 699-709.
Van der loos. et al. "The Animal Research Kit (ARK) Can Be Used in a Multistep Double Staining Method for Human Tissue Specimens", The Journal of Histochemistry & Cytochemistry, vol. 48, (10): 1431-1437 (2000).
Van der Loos, et al, "Multiple immunoenzyme staining techniques Use of fluoresceinated, biotinylated and unlabeled monoclonal antibodies", Journal of Immunological Methods, 117 (1989), pp. 45-52.
Van der loos. et al. "An Immunoenzyme Triple-staining Method Using Both Polyclonal and Monoclonal antibodies from the same Species. Application of combined direct, Indirect, and Avidin-Biotin Complex (ABC) Technique", The Journal of Histochemistry and Cytochemistry, vol. 35, No. 11, pp. 1199-1204 (1987).
Van der Loos, et al. "Practical suggestions for successful immunoenzyme double-staining experiments", Histochemical Journal (25), pp. 1-13 (1993).
Brunangelo Falin!, et al., "Double Labeled-Antigen Method for Demonstration of Intracellular Antigens in Paraffin-embedded Tissues", The Journal of Histochemistry and Cytochemistry. vol. 30, No. 1, pp. 21-26 (1982).
Data Sheet Fast Red Stubsrate Pack and Compponents for Use with Alakline Phosphatase Detection Kits & BioGenex Automated Staining Systems (Doc. No. HK180, Rev. No. F112) Jul. 1, 2003 accessed from web.archive.org/web/20030701115828/http://www.bioQenex.com/biOQenex h.html.
Vector Red Alkaline Phosphatase Substrate Kit I Cat. No. SK-5100, Oct. 31, 2000, accessed from web.archive.org/web/20031202200453/http://www.vectorlabs.com/protocols.asp.
Cordell et al, Journal of Histochemistry and Cytochemistry, 1984, vol. 32, No. 2 pp. 219-229 attached online version htte://jhc.sageeub.com/content/32/2/219.
Instructions for Universal Alkaline Phosphatase Immunostaining Kit (For Mouse and Rabbit Primary Antibodies) Cat. #KA-50F Apr. 7, 2003 Accessed from web.archive.org/web/20030407222427/http:I/dbiosys.com/new/index.asp?fuse=dsp cat&id=5.
Elias, Immunohistopathology—A Practical Approach to Diagnosis, 2nd Ed. , American Society for Clinical Pathology Press: Chicago, © 2003, p. 36.
Molinie, V. et. al., Mod. Pathol., 2004, 17, 1180.
Paner, GP, . et. al., Best Prac. In Diag. Immunohist.: Prostate, 2008, 132, 1388.
Rubin, MA et. al., JAMA, 2002,287, 1662.
Shah, RB et. al., Am. J. Surg. Path., 2002, 26, 1161.
Signoretti, Sabina 'p63 is a prostate basal cell marker and is required for prostate development'. Am J Pathol, vol. 157, No. 6, Dec. 2000, 1769-75.
Tacha, DE and Miller, RT, Appl. Immunohistochem. Mol. Morph . . . 2004, 12, 75.
Tavora. F and Epstein, JI, Am. J. Surg. Path., 2008, 32, 1060.
Yang, Yet. al., Am. J. Path., 1997, 150, 693.
Abrahams, NA, et. a f., Histopathology, 2002, 41, 35.
Adley, BP et. al., Am. J. Clin. Path., 2006, 126, 849.
Beach, R et. al., Am. J. Surg. Path., 2002, 26, 1588.
Bostwick, DG and Qian, J., Mod. Pathol., 2004, 17, 360.
DAKO Press Release Sep. 14, 2009, New Duoflex Cocktail Antibodies.
DAKO Screen Shot DuoFlex Cocktail, Anti-AMACR, Anti-Cytokeratin HMW, Anti-Cytoderatin 5/6: Oct. 5, 2009.
Herawi, M and Epstein, JI, Am. J. Surg. Path., 2007, 31, 889.
Jiang, Z et. al., Am. J. Clin. Path., 2004, 122, 275.
Jiang, Z et. al., Am. J. Clin. Path., 2005, 123,231.
Jiang, Z et. al., Am. J. Surg. Path., 2001, 25, 1397.
Luo, J et. al., Cancer. Res., 2002, 62, 2220.
Reis-Filho et al, Virchows Arch. (2003) vol. 443, pp. 122-132.
12 Pages from catalog: "product information form the Sigma-Aldrich Online Catalog" at sigmaaldrich.com/... ProductDetail.do?|...accessed Feb. 14, 2011.
8 Pages from catalog: "product information form the Sigma-Aldrich Online Catalog" at sigmaaldrich.com/ .. . / ProductDetail.do?|. .. accessed Feb. 16, 2011.
Epstein, JI, and Netto, GJ., Biopsy interpretation of the prostate, 2008, Lippincott, Williams & Wilkins: Philadelphia, p. 99.
BioSB p40 IHC of p40 on an FFPE Prostate Tissue, http://www.biosb.com/p40-page, Jul. 29, 2015, 4 pages.
Zeta Corporation IVD Data Sheet (Rev May 2014) p40 (Clone ZR8), 7 pages.
European Patent App. No. 14178215.1 Examination Report dated Dec. 15, 2015, 5 pages.
European Patent App. No. 14178215.1 Search Report dated Dec. 1, 2014, 11 pages.
Cartron, et al. Therapeutic activity of humanized anti-DC20 monoclonal antibody and polymorphism in IgG Fc receptor gene. www.bloodjournal.org, Jan. 21, 2016. 6 pages.
Creative Biolabs, Chimeric IgG construction; (c) 2007-2016 Creative Biolabs, 2 pages. Date Unknown.
Foran, James M. et al. European Phase II Study of Rituximab (Chimeric Anti-CD20 Monoclonal Antibody) for Patients with Newly Diagnosed Mantle-Cell Lymphoma and Previously Treated Mantle-Cell Lymphoma, Immunocytoma, and Small B-Cell Lymphocytic Lymphoma. Journal of Clinical Oncology, vol. 18, No. 2/317; Jan. 1, 2000, 7 pages.
Eng, Hui-Yan, et al. Enhanced antigen detection in immunohistochemical staining using a 'digitized' chimeric antibody. Oxford, Protein Engineering, Design & Selection, 2016, vol. 29 No. 1, pp. 11-21. Sep. 25, 2015, 11 pages.
Carter, Paul J. Potent antibody therapeutics by design. Nature Reviews, Immunology. vol. 6, May 2006. pp. 343-357. 15 pages.
European Patent App. No. 13841542.7. Extended European search report dated Apr. 28, 2016. 9 pages.

SEQUENCE LISTING

<160> NUMBER OF SEQ IDS NOS: 4

<210> SEQ ID NO 1
<211> LENGTH: 323
<212> TYPE: DNA
<213> ORGANISM: Mus musculus

<400> SEQUENCE: 1

```
tctgggggag gcttagtgca gcctggaggg tcccggaaac tctcctgtgc agcctctgga      60
ttcactttca gtagctttgg aatgcactgg gttcgtcagg ctccagagaa ggggctggag     120
tgggtcgcat acattagtag tggcagtagt accatctact atgcagacac agtgaagggc     180
cgattcacca tctccagaga caatcccaag aacaccctgt tcctgcaaat gaccagtcta     240
aggtctgagg acacggccat gtattactgt gcaagaaggt actactttga ctactggggc     300
caaggcacca ctctcacagt ctc                                             323
```

<210> SEQ ID NO 2
<211> LENGTH: 335
<212> TYPE: DNA
<213> ORGANISM: Mus musculus

<400> SEQUENCE: 2

```
gatattgtgc tgacacaatc tcctgcttcc ttagctgtat ctctggggca gagggccacc      60
atctcatgca gggccagcca aagtgtcagt acatctagct atagttatat gcactggtac     120
caacagaaac caggacagcc acccaaactc ctcatcaagt atgcatccaa cctagaatct     180
ggggtccctg ccaggttcag tggcagtggg tctgggacag acttcaccct caacatccat     240
cctgtggagg aggaggatac tgcaacatat tactgtcagc acagttggga gattccgtac     300
acgttcggag gggggaccaa gctggaaata aaacg                                335
```

<210> SEQ ID NO 3
<211> LENGTH: 319
<212> TYPE: DNA
<213> ORGANISM: Mus musculus

<400> SEQUENCE: 3

```
gatattgtgc tcacacagtc tccagcaatc atgtctgcat ctccagggga aaaggtcacc      60
atgacctgca gtgccagttc aagtgtaagt tacatgtact ggtaccagca gaagtcaagc     120
acctccccca aactctggat ttatgacaca tccaaactgg cttctggagt cccaggtcgc     180
ttcagtggca gtgggtctgg aaactcttac tctctcacga tcagcagcat ggaggctgaa     240
gatgttgcca cttattactg ttttcagggg agtgggtacc cactcacgtt cggctcgggg     300
acaaagttgg atataaaac                                                  319
```

<210> SEQ ID NO 4
<211> LENGTH: 15
<212> TYPE: PRT
<213> ORGANISM: Homo sapiens

<400> SEQUENCE: 4

```
Leu Ser Pro Ala Leu Thr Glu Ser Leu Leu Val Ala Leu Pro Pro
1               5                   10                  15
```

ANTI-UROPLAKIN II ANTIBODIES SYSTEMS AND METHODS

This application is the United States National Phase of International Patent Application Number PCT/US2013/062043 filed 26 Sep. 2013 which claims priority to and the benefit of U.S. Provisional Application No. 61/706,312 filed Sep. 27, 2012, each application hereby incorporated by reference herein in its entirety.

TECHNICAL FIELD

This invention relates to novel anti-Uroplakin II antibodies, compositions, cocktails, and kits comprising the antibodies and methods for using the antibodies.

BACKGROUND OF THE INVENTION

Microscopic examination of tissue samples, particularly those obtained by biopsy, is a common method for diagnosis of disease. In particular, immunohistochemistry (IHC), a technique in which specific antibodies are used to detect expression of specific proteins in the tissue sample, is a valuable tool for diagnosis, particularly for the detection and diagnosis of cancer.

Uroplakins ("UP" or "Ups") comprise a group of 4 transmembrane proteins (UPs Ia, Ib, II, and III) expressed in the luminal surface of normal urothelial superficial (umbrella) cells, which are specific differentiation products of urothelial cells. Uroplakin II ("UP II") may be a 15 kDa protein component of the urothelial plaques which may enhance the permeability barrier of the urothelium. The expression of UP II may be aberrant in urinary bladder transitional cell carcinoma ("TCC") of the bladder and thus may make it a useful marker for the diagnosis of cancer. The Wu et al. reference includes discussion of UP II mRNA as a promising diagnostic marker for bladder cancer and perhaps even micrometastases of bladder cancer in the pelvic lymph nodes (see article, "Uroplakin II as a promising marker for molecular diagnosis of nodal metastases from bladder cancer: comparison with cytokeratin 20." Wu X, Kakehi Y, Zeng Y, Taoka R, Tsunemori H, Inui M. J Urol. 2005 December; 174(6):2138-42, hereby incorporated by reference herein.) UP II mRNA was detected in 19 of 19 (100%) and 15 of 16 (93.8%) bladder tumor tissue specimens and pelvic lymph node samples with metastasis, respectively. On the other hand, UP II mRNA was detected in only 6 cases out of 66 (10%) pelvic lymph node samples without metastasis. Therefore, positive expression of UP II mRNA may indicate nodal metastases from bladder cancer. It may be important to determine the nodal metastases in patients with bladder cancer after radical cystectomy as this subpopulation of patients may urgently need postoperative chemotherapy to survive. The authors conclude that the detection of UP II mRNA may improve clinical outcome following radical cystectomy perhaps by providing helpful information in the diagnosis and management of TCC. It is desirable, therefore, for development of an anti-UP II antibody for detection of UP-II protein expression in the tissues of patients such as with TCC or the like.

Studies have shown UP II mRNA to be expressed in bladder tissues and peripheral blood of patients with primary and metastatic TCCs, perhaps suggesting its potential role as a biomarker for urothelial carcinomas. The clinical usefulness of UP II may have been recognized from these studies perhaps solely based on its mRNA data. Additional investigations characterizing the protein localization of UPII in TCC may be warranted, especially when the protein molecules may be more stable than mRNA molecules. One study employed a pan-UP antibody which may have reacted with all UPIb, UPII, and even UPIII isoforms perhaps to demonstrate the persistent expression of UP in advanced urothelial carcinomas; however, the specific UP II protein level could not be determined using this pan-UP antibody. (See, Persistent Uroplakin Expression in Advanced Urothelial Carcinomas: Implications in Urothelial Tumor Progression and Clinical Outcome. Hong-Ying Huang, Shahrokh F. Shariat, Tung-Tien Sun, Herbert Lepor, Ellen Shapiro, Jer-Tsong Hsieh, Raheela Ashfaq, Yair Lotan, and Xue-Ru Wu, Hum Pathol. 2007 November; 38(11): 1703-1713, hereby incorporated by reference herein). Little may be known about the protein expression of UP II in urothelial cancer, possibly due to the absence of a specific anti-UP II antibody.

A clear need exists for a sensitive and even specific anti-Uroplakin II antibody for use in cancer diagnosis. Anti-UP III antibodies have been previously developed as markers for carcinoma of urothelial origin. Here the present invention provides an anti-UP II antibody [clone BC21] which may be highly specific and may even be more sensitive than the anti-UP III antibody [clone BC17]. In cases of TCC, an example of the present invention provides an anti-UP II antibody that exhibited an increased sensitivity (about 46/59, about 78%) compared to the anti-UP III antibody (about 33/59, about 56%). Perhaps in addition to its stronger staining profile, the anti-UP II antibody [BC21] may exhibit a wider localization pattern compared to anti-UP III antibody. This could be due to the superior sensitivity of the anti-UP II antibody or perhaps even the two isoforms may have distinct roles in the formation of urothelial plaques. The difference in their function may not be fully known; however, mice lacking the UP II gene showed no urothelial plaque formation while mice lacking the UP III gene may still retain small urothelial plaques. If UP II and UP III indeed exhibit non-overlapping functions, determination of either isoform may not be sufficient for an effective diagnosis of TCC. Therefore, an anti-UP II antibody may be needed for a more complete coverage of protein expression of UP isoforms.

The development of an anti-UP II antibody may aid in the diagnosis of primary and even metastatic TCCs, may aid in the verification of UP II mRNA expression perhaps in previous clinical studies, and may even aid in distinguishing a protein expression of UP II versus UP III. New anti-Uroplakin II antibodies such as anti-Uroplakin II antibody [BC21] with perhaps increased staining sensitivity, and perhaps even while preserving equal or even superior staining specificity such as compared to anti-Uroplakin III antibody [BC17], have been provided in the present invention.

DISCLOSURE OF THE INVENTION

General embodiments of the present invention may include monoclonal antibodies for recognizing UP II, methods for their preparation, use in immunohistochemistry, or the like. In embodiments, anti-UPII antibody clones such as the anti-UP II antibody clone BC21 can be obtained by immunizing Balb/C mice with a recombinant human UP II protein corresponding to amino acids 26-155, obtained by *E. coli* expression. The UP II proteins may be injected into the BALB/c mice, with an adjuvant, via intraperitoneal injections, perhaps about 5 times at about three week intervals. The immune reactivity to UP II may be assessed by direct ELISA on recombinant UP II protein. Mice with the highest titer may be chosen for developing hybridomas by cell fusion. A hybridoma clone demonstrating the best reactivity to UP II on human tissues may be chosen and may be designated as BC21. The BC21 clone may be tested for isotype and may be identified as a mouse IgG1/kappa. The BC21 antibody may be produced by large scale tissue culture of the hybridoma cells and by ascites in BALB/c mice. The supernatant and antibody ascites may be collected and the antibody may be purified by Protein A affinity column. BC21 demonstrated specific reactivity to human UP II protein by ELISA, Western blotting, and even human tissues.

Anti-UPII antibodies such as the mouse monoclonal anti-UP II antibody BC21 may be useful for the detection of UP II in tissue samples, perhaps with several significant, but unexpected advantages over currently known anti-UP III antibodies. When used in traditional immunohistochemistry procedures, anti-UPII antibodies such as the mouse anti-UP II antibody BC21 may result in membrane or cytoplasmic staining of UP II with a specificity perhaps similar to that of known anti-UP III antibodies. However, anti-UPII antibodies such as BC21 may exhibit increased sensitivity, perhaps as compared to past anti-UP III antibodies, which may offer significant improvements. With anti-UPII antibodies such as BC21, analysis of the sample may be simplified and UP II expression in tumor cells may be readily identifiable, allowing diagnosis in cases that may otherwise be difficult, or not even possible, to diagnose.

MODE(S) FOR CARRYING OUT THE INVENTION

Figure 1:
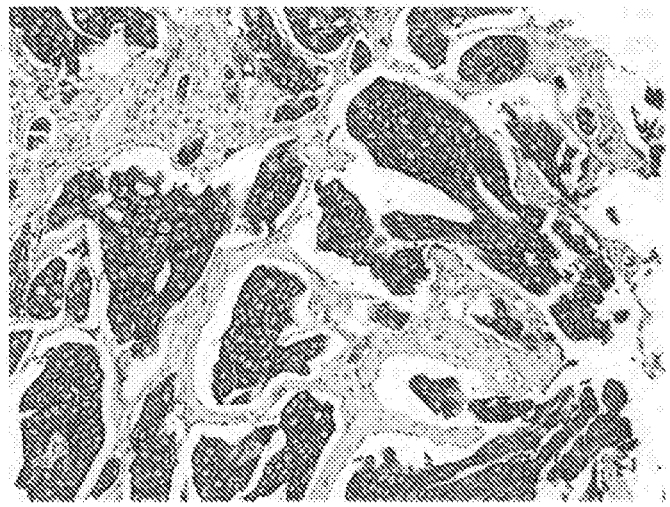
FIG. 1 shows an example of anti-UP II antibody [BC21] staining on bladder TCC tissue (grade 3).

As may be understood from the earlier discussion, the present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

Embodiments of the present invention may provide antibodies and methods thereof that specifically bind to UP II and may be used for the detection of UP II in the diagnosis for several types of cancers. An antibody may be an antibody fragment, a mouse monoclonal antibody, a chimeric antibody, a humanized monoclonal antibody, a human monoclonal antibody, an antibody with a label attached or even conjugated therewith or with a fragment thereof, an antibody labeled with a detectable signal or stain, an antibody labeled with a toxin, or the like. A label may include but is not limited to radioactive element, magnetic particles, radioisotope, fluorescent dye, enzyme, toxin, signal, stain, detection enzymes, horseradish peroxidase (HRP), alkaline phosphatase (AP), beta-galactosidase, chromogens, Fast Red, 3,3'-diaminobenzidine, 3-amino-9-ethylcarbazole, 5-bromo-4-chloro-3-indolyl phosphate, 3,3',5,5'-tetramethylbenzidine, 5-bromo-4-chloro-3-indolyl-β-D-glucuronide, any combination thereof, or the like. Systems and methods of the present invention may relate to the antibody or its antigen binding portion capable of binding to UP II.

Embodiments of the present invention may provide monoclonal antibodies and methods thereof that specifically bind to UP II and may be used for the detection of UP II in the diagnosis for several types of cancers. The monoclonal antibody may be an antibody fragment, a mouse monoclonal antibody, a rabbit monoclonal antibody, a chimeric antibody, a humanized monoclonal antibody, a human monoclonal antibody, an antibody labeled with a detectable signal or stain, an antibody labeled with a toxin, or the like. Systems and methods of the present invention may relate to the monoclonal antibody or its antigen binding portion capable of binding to UP II.

Mouse monoclonal antibodies may be commonly used in immunoassay methods to identify specific analytes, including as primary antibodies in immunohistochemistry procedures. Mouse monoclonal antibodies specific for the protein target of interest can be produced using generally known procedures. Generally, exposing a mouse to the antigen of interest (e.g. a peptide fragment of the desired target or the full-length protein target) may induce an immune response in which the mouse generates multiple antibodies that bind the antigen, each of which may be produced by a particular B-cell. These B-cells may be isolated from the mouse spleen and the antibodies produced may be evaluated for their suitability as primary antibodies in IHC. After selecting the optimal antibody, the associated B-cell may be fused with a tumor cell using known procedures, perhaps resulting in a hybridoma, a new cell line that can endlessly replicate and may continuously produce the desired antibody.

Monoclonal antibodies may be preferred over polyclonal antibodies for several reasons. In particular, monoclonal antibodies may be derived from a single B-cell and as such may recognize a single epitope, perhaps resulting in greater specificity. Monoclonal antibodies may also be conveniently and reproducibly generated in cell culture, perhaps resulting in a constant supply of the desired antibody. Of course, polyclonal antibodies may be used in some embodiments.

Anti-UPII antibodies such as a mouse monoclonal anti-UP II antibody BC21 may be produced using these general procedures and may be evaluated by immunohistochemistry for sensitivity and specificity on a variety of normal and neoplastic tissues, perhaps particularly in comparison to the previously known anti-UP III antibody [BC17].

Example of UPII Protein Expression

A UPII recombinant protein from amino acid sequence 26 to 155 may be cloned and expressed from *E. coli*. Briefly, UPII cDNA may be cloned and purified. The UPII cDNA may be digested by restriction enzymes and ligated into the pET30a-GST vector. BL21 cells may be transformed with the construct. The colonies expressing the correct size of recombinant protein may be selected and sequenced. A further scale up production may be performed by culturing the *E. coli* in LB media containing 0.5 mM IPTG. The final UPII recombinant protein may be purified and analyzed by SDS-PAGE.

Example of Host Immunization

Female BALB/c (about 6 to about 8 weeks old) mice may be immunized intraperitoneally (i.p.) with about 100 µg human UPII protein per mouse in complete Freund's adjuvant. About three weeks later, the mice may be boosted with another 100 µg human UPII per mouse in incomplete Freund's adjuvant about 4 more times in about 3 week intervals. Mice may be bled from the tails, and sera may be collected and stored at −20° C. for later analysis of antibody titers by enzyme-linked immunosorbent assay (ELISA).

Example of Hybridomas

Hybridomas producing antibodies to UPII may be generated by standard techniques from splenocytes of UPII-immunized BALB/c mice. For example, splenocytes from UPII-immunized mice may be fused to P3-X63-Ag 8.653 myeloma cells (non-secreting myeloma derived from SP2/0 Balb/c myeloma cells) by incubation with about 50% polyethylene glycol at a ratio of about 4:1. Following incubation, cells may be pelleted by centrifugation perhaps at about 300×g for about 10 minutes, washed in about 25 ml of PBS, recentrifuged, and cell pellet may be resuspended in about 100 ml of fresh Dulbecco's Medium containing about 20% fetal bovine serum (Hyclone, Utah, Co). Aliquots of about 100 µl can be added to each well of ten 96-well microtiter plates (Corning, Lowell, Mass.). About twenty four hours later, about 100 µl DMEM culture medium supplemented with about 1M hypoxanthine (HT), about 4 mM aminopterin and about 160 mM thymidine (HAT) can be added to each microtiter well. Media may be replaced perhaps after about 4 days with complete media (perhaps containing HAT and HT). Over the following about 10 days, media may be removed and replaced with fresh media with reduced or perhaps even no HAT and HT added. Hybridoma supernatants may be screened by ELISA for antibody reactivity to UPII, and hybridoma clones may then be selected and stabilized perhaps by cloning twice by limiting dilution.

Hybridoma cells referred to as Anti-human UPII hybridoma clone BC21 have been deposited with the American Type Culture Collection (ATCC) under ATCC Patent Deposit Designation No. PTA-13181. Embodiments of the present invention may provide an antibody or fragment thereof produced by the hybridoma deposited at the ATCC and may even include a method for producing a monoclonal antibody by culturing the hybridoma cell which produces the monoclonal antibody capable of specifically recognizing Uroplakin II and even allowing the hybridoma to produce monoclonal antibodies.

ELISA:

Host anti-sera immune responses to UPII may be measured by ELISA. For example, a solution of UPII (about 1 µg/ml) in phosphate-buffered saline (PBS) may be used to coat about 96-well flat bottom polystyrene plates. The plates may then be blocked with about 1% bovine serum albumin (BSA)-PBS. Either diluted immune sera or hybridoma supernatants may be added and incubated at about 37° C. for about 1 hour. After washing the plates with PBS, the plates may be incubated with goat anti-mouse-HRP reagents (Jackson Labs). Incubations may be done at about 37° C. for about 30 minutes. ABTS substrate may be added to develop color and the absorbance at about 405 nm (A405) may be measured in a microtiter plate reader.

Isotype of Monoclonal Antibodies:

Anti-UPII antibodies such as the BC21 monoclonal antibody may be isotyped using a mouse monoclonal antibody isotyping kit (Invitrogen, Carlsbad Calif.). For example, about 100 µl of supernatant from mouse monoclonal antibody [BC21] cells may be added to the plate coated goat anti mouse IgG1, IgG2A, IgG2B, IgG3, IgM, and IgA. After about 30 minutes incubation, the plate may be washed 3 times with PBS and may be incubated with goat anti mouse Ig-HRP reagent. ABTS substrate may be added to develop color and the absorbance at about 405 nm (A405) may be measured in a microtiter plate reader. The BC21 clone may be tested for isotype and may be identified as a mouse IgG1/kappa.

Antibody Production and Purification:

The selected hybridoma cells from clone BC21 may be cultured with DMEM culture medium supplemented with about 10% FBS or any serum-free medium. The culture supernatants may be further purified by protein A affinity column. The hybridoma cells may also be injected into pristane-primed BALB/c mice to produce antibody ascites. The antibody ascites may be further purified by protein A affinity column. IgG concentration may be measured spectrophotometrically using the extinction coefficient for human IgG of about 1.4 (about 0.1% at about 280 nm). The purity of IgG may be determined by SDS-PAGE.

Cross-Reactivity Tested by Western Blotting:

The purified monoclonal antibody [BC21] may be characterized by Western Blotting. Full-length UPII or UPIII protein may be subjected to protein gel electrophoresis using about 4 to about 12% SDS-PAGE with Tris-glycine buffer and may be transferred onto nitrocellulose filters in Tris-glycine buffer. Proteins on the blots may be visualized by incubating the BC21 antibody for about 60 minutes in room temperature after blocking with blocking buffer, perhaps followed by incubating with peroxidase-conjugated goat anti-mouse immnoglobulins.

Determination of VH and VL Sequences:

Total RNA may be extracted from hybridomas using Qiagen kit (USA, Gaithersburg, Md.) as per the manufacturer's instructions. First-round RT-PCR may be carried out with QIAGEN® OneStep RT-PCR Kit. RT-PCR may be performed with primer sets specific for the heavy and light chains. For each RNA sample, about 12 individual heavy chain and about 11 light chain RT-PCR reactions can be set up using degenerate forward primer mixtures covering the leader sequences of variable regions. Reverse primers may be located in the constant regions of heavy and light chains. Restriction sites may not be engineered into the primers. The RT-PCR products from the first-round reactions may be amplified in the second-round PCR. About 12 individual heavy chain and about 11 light chain RT-PCR reactions can be set up using semi-nested primer sets specific for antibody variable regions. The amplified cDNAs can be gel purified and may then be sequenced.

[BC21] Variable Domains were sequenced to provide isolated polynucleotides that comprise nucleic acid sequences encoding the amino acid sequences of one or more of the CDRs of the light and/or heavy chain variable regions of a monoclonal antibody described herein that binds to the UP II epitope LSPALTESLLVALPP identified as SEQ ID NO: 4. The sequence of the variable region of the heavy chain is identified as SEQ ID NO: 1 and the sequence of the variable region of the light chain is identified as SEQ ID NO: 2 or SEQ ID NO: 3. An antibody or fragment thereof may include a polypeptide of the amino acid sequence encoded by the nucleic acid sequence of SEQ ID NO: 1 and/or SEQ ID NO: 2 and/or SEQ ID NO: 3. An antibody or fragment thereof may include a light chain variable region having an amino acid sequence encoded by the nucleic acid sequence of SEQ ID NO: 2 and/or SEQ ID NO: 3 and may even include a heavy chain variable region having an amino acid sequence encoded by a nucleic acid sequence of SEQ ID NO: 1. An antibody or fragment thereof may specifically bind to at least one polypeptide of an amino acid sequence of SEQ ID NO: 4. As mentioned herein, a fragment thereof may include an antigen binding fragment thereof.

In embodiments, an antibody or fragment thereof, or even an isolated and purified nucleic acid sequence may have an amino acid sequence of at least about 70% identical to an amino acid sequence encoded by a nucleic acid sequence of SEQ ID NO: 1 and/or SEQ ID NO: 2 and/or SEQ ID NO: 3. An antibody or fragment thereof may specifically binds to at least one polypeptide with an amino acid sequence that is at least about 70% identical to residues of SEQ ID NO: 4. Other percentages may include, but are not limited to, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, and perhaps even at least about 99%, or the like.

Epitope Mapping of the Mouse Anti-UPII [BC21] Binding Sequence:

In order to determine the peptide sequence of UP II that is recognized by anti-UPII antibodies such as BC21, epitope mapping may be conducted perhaps using two assays: direct ELISA and even dot blot. In an ELISA assay, the sensitivity and specificity of the anti-UP II [BC21] antibody may be determined by measuring the antibody titer at about 1:500 and about 1:1000. Overlapping peptides at a length of about 15 amino acids each, covering the human UP II protein sequence from perhaps 26 to 155 amino acids, may be used to determine the preferred sequence of BC21 binding.

The epitope for BC21 was shown to be included in the residues 36-50 amino acids of UPII, which is LSPAL-TESLLVALPP identified as SEQ ID NO: 4. The epitope of the mouse monoclonal UPII antibody, or a portion thereof, may be a useful antigen for the production of new monoclonal antibodies, including production in species other than mouse (e.g. rabbit, goat, horse, chicken, etc.). Of course, a polyclonal antibody may specifically bind to an epitope in SEQ ID NO: 4 which relates to residues 36-50 of the Uroplakin II protein.

For direct ELISA protocol, the plates may be first coated with about 100 µl of UP II peptides at about 5 µg/mL in coating buffer (pH about 9.5) overnight at about 4° C., followed by blocking (about 3% BSA) at about 200 µl/well for about 1 hour at room temperature. The plates may be incubated with purified UP II antibody at about 100 ng/mL and about 200 ng/mL separately for about 1 hour at about room temperature on an ELISA-plate shaker. Then the plates may be washed perhaps five times with PBST (about 300 µl/well) followed by the addition of goat anti-mouse IgG-HRP to the plates and incubation for about 1 hour on a plate-shaker. The plates may then be washed with PBST (about 300 µl/well) and blotted to dry, and TMB may be added at about 100 µl/well, developed for about 5 min on a shaker, and may even be followed by a stop solution (about 50 µl/well). Absorbance may be measured at about 450 nm on an ELISA plate reader perhaps according to the manufacturer's recommendation.

For the dot blot assay, a nitrocellulose membrane may be blotted with about 1 µl at a concentration of about 1 mg/ml the peptide, quadruplicates per peptide. This membrane may be incubated for about 1 hour at room temperature until it may be completely dry. The membrane may be blocked with about 3% BSA in TBST (e.g., about 50 mM Tris, about 0.5 M NaCl, about 0.05% Tween-20, pH about 7.4) for about 1 hour at room temperature, then mouse anti UP II antibody [BC21] may be added at about 200 ng/ml for about 1 hr at RT in TBST. Then the membrane may be washed for about 3 times (about 10 minutes each) in TBST on an orbital shaker, followed by incubating with secondary antibody goat anti mouse IgG1-AP for about 1 hour at room temperature in TBST. The membrane may be washed perhaps about 3 times (about 10 minutes each) in TBST on a rocker. The binding may be detected by adding Western Glo Chemiluminescent detection reagents and exposing to film.

IHC Method with Anti-UP II BC21:

Immunohistochemistry using anti-UPII antibodies such as the mouse monoclonal anti-UP II antibody BC21 may be performed on formalin-fixed paraffin embedded (FFPE) tissue samples using procedures generally known to those in the art, as generally exemplified by the following non-limiting examples (e.g., washes with Tris-buffered saline, pH about 7.6, between steps):

1) Sections (~5 µm) of formalin fixed paraffin-embedded tissues may be mounted on commercially available microscope slides perhaps coated with polylysine.
2) Sections may be deparaffinized (using xylenes or a xylene-substitute) and may be rehydrated perhaps through a series of alcohol/water solutions, perhaps followed by blocking of endogenous peroxidases perhaps with about 3% hydrogen peroxide solution.
3) Samples may be subjected to heat-induced antigen retrieval using a citrate buffer in a pressure cooker (Reveal, Decloaking Chamber; Biocare Medical) and may be heated to about 125° C. for about 30 seconds. [Other antigen retrieval methods known to those skilled in the art (e.g., steamer, microwave oven, enzyme, or the like) may also be acceptable.] Tissues may be allowed to cool for about 10 minutes and then may be rinsed with deionized water.

4) The UP II antibody BC21 may be applied in a phosphate-buffered solution (pH about 6.0) with bovine serum albumin as carrier protein for about 30 minutes.
5) Detection of the UP II antibody perhaps with a horseradish peroxidase (HRP) conjugated secondary antibody (MACH 4 Universal HRP-Polymer Detection, Biocare Medical) may be accomplished in two steps. An initial application of a rabbit anti-mouse IGg antibody for about 10 minutes may be followed by incubation with a goat anti-rabbit-HRP conjugate for about 10 minutes.
6) In perhaps a final detection step, 3,3'-diaminobenzidine (DAB) in buffer perhaps containing about 0.02% hydrogen peroxide (Betazoid DAB, Biocare Medical) may be applied. The oxidation of DAB through an HRP-mediated mechanism may result in precipitation of a brown, chromogenic product, perhaps allowing identification of sites of UP II expression.
7) Slides may be briefly counterstained perhaps in a modified Mayer's hematoxylin.

Results of IHC Staining with Mouse Monoclonal Anti-UP II Antibody BC21:

Using the above protocol, a variety of normal and neoplastic tissues were evaluated for UP II expression using BC21 and compared to staining patterns using a mouse monoclonal anti-UP III antibody (BC17, Biocare Medical). Both antibodies were optimized for titer (e.g., concentration) using methods well known to those in the art. For example, various antibody titers were evaluated to maximize staining intensity, perhaps while minimizing or even eliminating background staining. For each antibody, the titer that provided the maximum staining intensity, perhaps with the minimal background staining, was used.

FIGS. 1-8 shows several examples of staining of bladder transitional cell carcinoma by anti-UP II antibody (BC21), in comparison to staining with anti-UP III antibody (BC17), on a serial section of the same specimen.

Table 1 shows the sensitivity of anti-UP II antibody (BC21) staining 178 specimens of bladder cancer (e.g., transitional cell carcinoma (TCC) and papillary TCC), using a tissue microarray (TMA). Employing a cut-off of ≥about 5% of tumor cells staining as the criteria to determine a case as "positive" for UP II, and conversely <about 5% of tumor cells staining as the criteria to determine a case "negative," 137 of 178 (about 77%) were found to be positive for UP II (BC21). Diagnosis of tumors of higher grade can sometimes be a challenge. In these specimens, anti-UP II antibody (BC21) identified 68 of 83 (about 82%) of Grade II tumors, and 25 of 44 (about 57%) of Grade III tumors.

TABLE 1

Anti-UP II Antibody (BC21) on Bladder cancer (TCC and Papillary TCC) TMA

| Grade | Number of Specimens | Number of Positive Specimens | % Positive | Number of Negative Specimens | % Negative |
|---|---|---|---|---|---|
| Grades I, II & III | 178 | 137 | 77% | 41 | 23% |
| Grade II | 83 | 68 | 82% | 15 | 18% |
| Grade III | 44 | 25 | 57% | 19 | 43% |

The greater sensitivity of anti-UP II antibody (BC21), compared to anti-UP III antibody (BC17), was demonstrated by staining the same 59 specimens of TCC of Grades I, II and III with each antibody (Table 2). Using the same criteria, anti-UP II antibody (BC21) identified 46 specimens as positive (about 78%), compared to 33 specimens (about 56%) determined to be positive with anti-UP III antibody (BC17). In Grade II specimens, anti-UP II antibody (BC21) and anti-UP III antibody (BC17) demonstrated sensitivities of about 77% (27 of 35) and about 54% (19 of 35), respectively. In Grade III specimens, anti-UP II antibody (BC21) and anti-UP III antibody (BC17) demonstrated a similar sensitivity of about 64% (7 of 11). In many comparisons, anti-UP II antibody (BC21) provided a darker staining than anti-UP III antibody (BC17).

TABLE 2

Comparison of anti-UP II antibody (BC21) and anti-UP III antibody (BC17) on Bladder cancer (TCC and Papillary TCC) TMA

| Antibody | Grade | Number of Specimens | Number of Positive Specimens | % Positive | Number of Negative Specimens | % Negative |
|---|---|---|---|---|---|---|
| BC21 | Grades I, II & III | 59 | 46 | 78% | 13 | 22% |
| BC17 | Grades I, II & III | 59 | 33 | 56% | 26 | 44% |
| BC21 | Grade II | 35 | 27 | 77% | 8 | 23% |
| BC17 | Grade II | 35 | 19 | 54% | 16 | 46% |
| BC21 | Grade III | 11 | 7 | 64% | 4 | 36% |
| BC17 | Grade III | 11 | 7 | 64% | 4 | 36% |

Anti-UP II antibody (BC21) may be highly specific perhaps when evaluated on a variety of normal (Table 3) and even neoplastic (Table 4) tissues. Bladder and ureter may be the only normal tissue to stain positive with UP II (BC21). Such staining may be expected, perhaps considering that the known expression of UP II in normal urothelium anti-UP II antibody (BC21) may not stain any other normal or neoplastic tissues, which may demonstrate its high specificity.

TABLE 3

Anti-UP II antibody (BC21) staining of normal tissues

| Tissue | # cases | Number of positive cases |
|---|---|---|
| Adrenal gland | 3 | 0 |
| Bladder | 7 | 5 |
| Bone marrow | 1 | 0 |

TABLE 3-continued

Anti-UP II antibody (BC21) staining of normal tissues

| Tissue | # cases | Number of positive cases |
|---|---|---|
| Eye | 2 | 0 |
| Breast | 3 | 0 |
| Cerebellum | 3 | 0 |
| Cerebral cortex | 3 | 0 |
| Fallopian tube | 3 | 0 |
| GI-Esophagus | 3 | 0 |
| GI-Stomach | 3 | 0 |
| GI-Small intestine | 3 | 0 |
| GI-Colon | 3 | 0 |
| GI-Rectum | 3 | 0 |
| Heart | 3 | 0 |
| Kidney | 6 | 0 |
| Liver | 3 | 0 |
| Lung | 3 | 0 |
| Ovary | 3 | 0 |
| Pancreas | 3 | 0 |
| Parathyroid | 1 | 0 |
| Pituitary gland | 2 | 0 |
| Placenta | 3 | 0 |
| Prostate | 3 | 0 |
| Skin | 2 | 0 |
| Spinal cord | 2 | 0 |
| Spleen | 2 | 0 |
| Striated muscle | 3 | 0 |
| Testis | 3 | 0 |
| Thymus | 3 | 0 |
| Thyroid | 3 | 0 |
| Tonsil | 3 | 0 |
| Ureter | 3 | 3 |
| Uterus-cervix | 3 | 0 |
| Uterus-endometrium | 3 | 0 |

TABLE 4

Anti-UP II antibody (BC21) staining of various tumor tissues

| Tumor Type | Number of cases | Number of Positive Cases |
|---|---|---|
| Prostate cancer | 10 | 0 |
| Lung cancer | 20 | 0 |
| Breast cancer | 10 | 0 |
| Colon cancer | 30 | 0 |
| Renal cancer | 5 | 0 |

Figure 2:
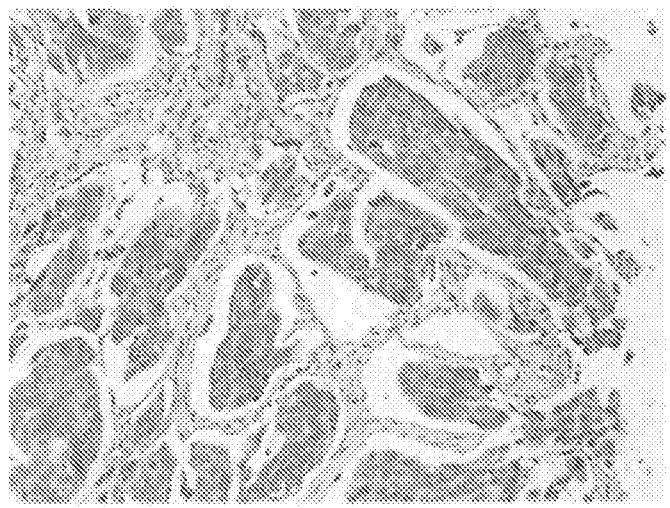
FIG. 2 shows an example of anti-UP III antibody [BC17] staining on a serial section of the same bladder TCC tissue of FIG. 1.
Figure 3:
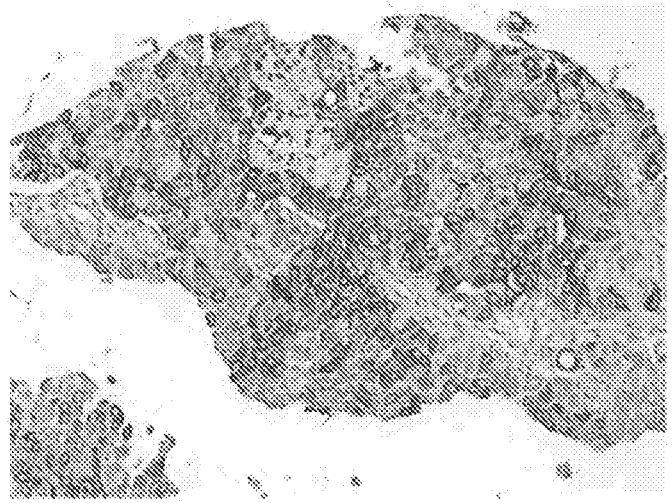
FIG. 3 shows an example of anti-UP II antibody [BC21] staining on bladder TCC tissue (grade 2).
Figure 4:
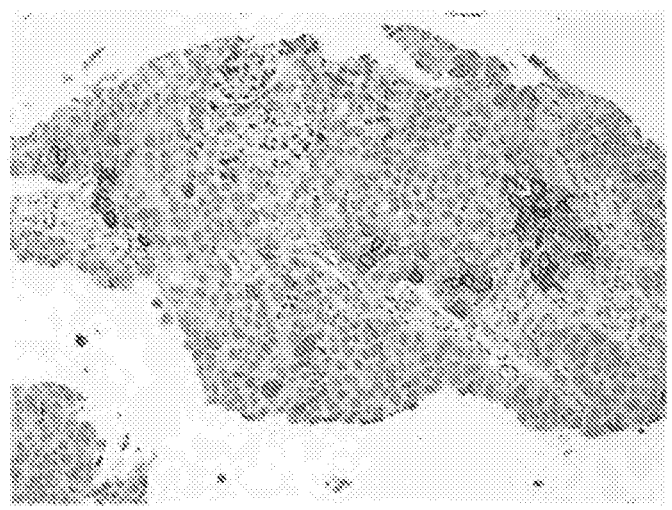
FIG. 4 shows an example of anti-UP III antibody [BC17] staining on a serial section of the same bladder TCC tissue of FIG. 3.
Figure 5:
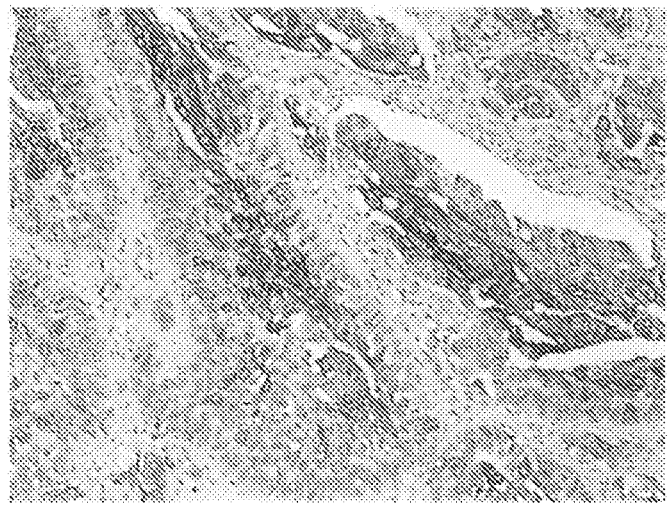
FIG. 5 shows an example of anti-UP II antibody [BC21] staining on bladder TCC tissue (grade 3).
Figure 6:
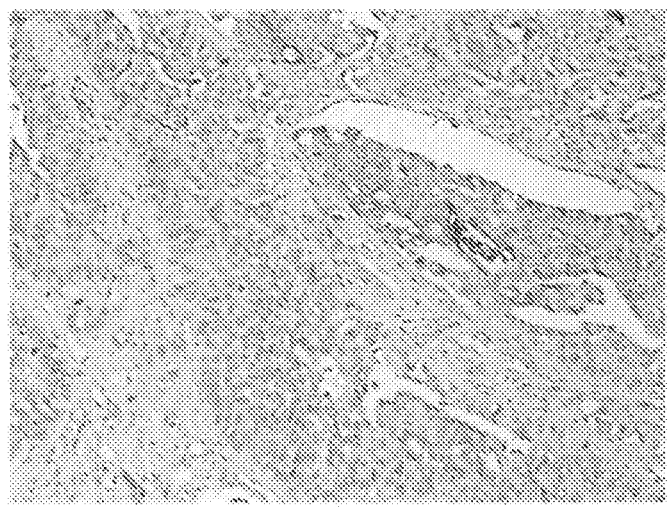
FIG. 6 shows an example of anti-UP III antibody [BC17] staining on a serial section of the same bladder TCC tissue of FIG. 5.
Figure 7:
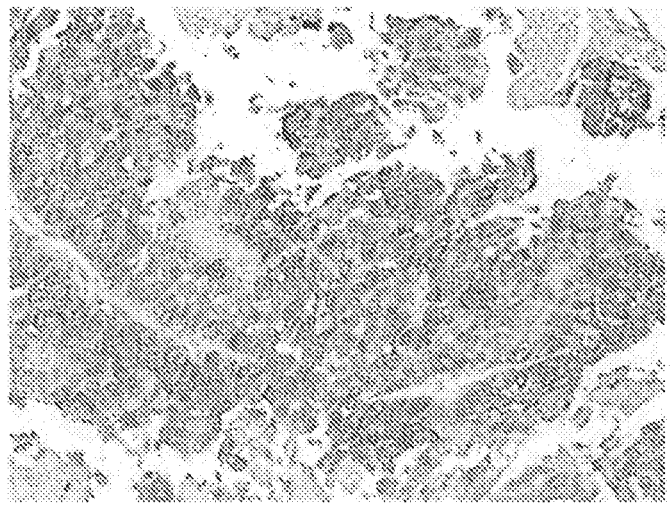
FIG. 7 shows an example of anti-UP II antibody [BC21] staining on bladder TCC tissue (grade 3).
Figure 8:
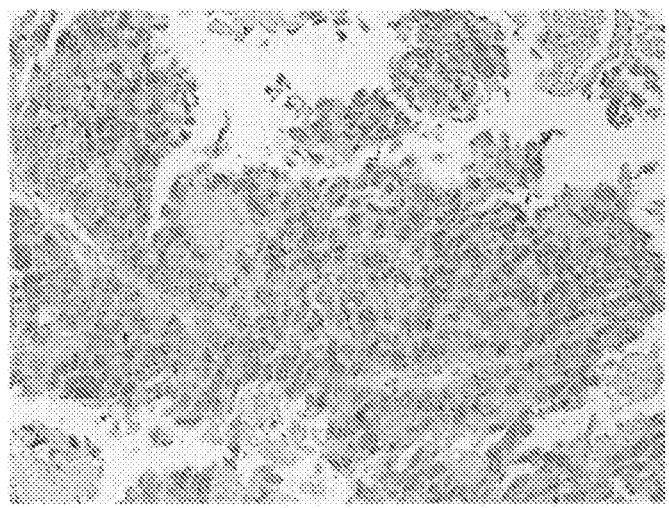
FIG. 8 shows an example of anti-UP III antibody [BC17] staining on a serial section of the same bladder TCC tissue of FIG. 7.

Anti-UPII antibodies such as the monoclonal mouse anti-UP II antibody (BC21) may offer distinct advantages with its improved sensitivity, perhaps even as compared to monoclonal mouse anti-UP III antibody (BC17). FIGS. 1-8 show examples of comparisons of BC21 with BC17 staining serial sections of the same specimen of bladder TCC, perhaps demonstrating the greater sensitivity of BC21. For example, the specimen of FIGS. 1 and 2 may exhibit strong membrane and cytoplasmic staining with BC21 (FIG. 1), while the staining of BC17 may be minimal in this case (FIG. 2). In FIGS. 3 and 4, a strong and widespread staining of BC21 may be observed (FIG. 3); whereas only sparse, focal staining may be observed on the same specimen with BC17 (FIG. 4). Similarly, the specimen of FIGS. 5 and 6 may display strong staining with BC21 (FIG. 5), but may have only limited staining with BC17 (FIG. 6). Finally, FIGS. 7 and 8 show a specimen that may also exhibit a strong staining with BC21 (FIG. 7); in contrast, BC17 may be negative on this same specimen (FIG. 8).

These examples demonstrate cases where a pathologist may have been able to definitively identify the presence of urothelial carcinoma with an anti-UP II antibody such as BC21, which would not have been possible with a less sensitive antibody, such as with BC17 (FIGS. 1, 2, 7 and 8). Or, the ambiguous results with an anti-UP III antibody, such as BC17 may have led to an equivocal diagnosis that lacks confidence, whereas an anti-UP II antibody, such as BC21, may offer a clear, unambiguous result (FIGS. 3, 4, 5 and 6).

The minimal staining observed with BC17 in FIGS. 3, 4, 5 and 6 may provide excellent examples of the challenge that may be faced by pathologists when using a less sensitive antibody; specifically, when the staining observed may be sparse and light, it may be difficult to determine with confidence if this is true positive staining, signaling the presence of UP II and perhaps indicative of urothelial carcinoma, or if it is a misleading staining artifact and should be dismissed. The ambiguity associated with a less sensitive antibody may lead to equivocal, or even incorrect diagnoses and patients with urothelial carcinoma may not receive appropriate treatment in a timely fashion. In contrast, an anti-UP II antibody, such as BC21, may offer a significant advantage for diagnosis with its increased sensitivity. An anti-UP II antibody, such as BC21, may result in strong, clear staining of urothelial carcinoma that may allow a pathologist to definitively return a diagnosis of urothelial carcinoma, perhaps allowing a patient to expeditiously receive the most appropriate treatment.

Results of Western Blots with Mouse Monoclonal Anti-UP II Antibody BC21

Figure 9A:
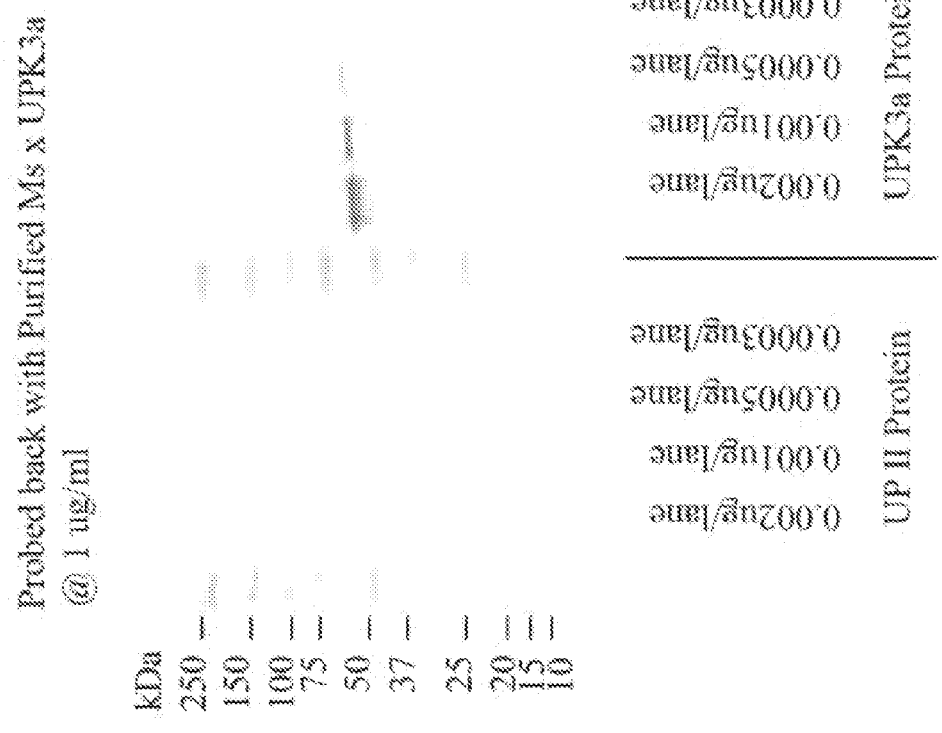
FIGS. 9A and 9B show the cross-reactivity of BC21 and BC17 antibodies with Uroplakin II protein and Uroplakin III protein by Western blot.
Figure 9B:
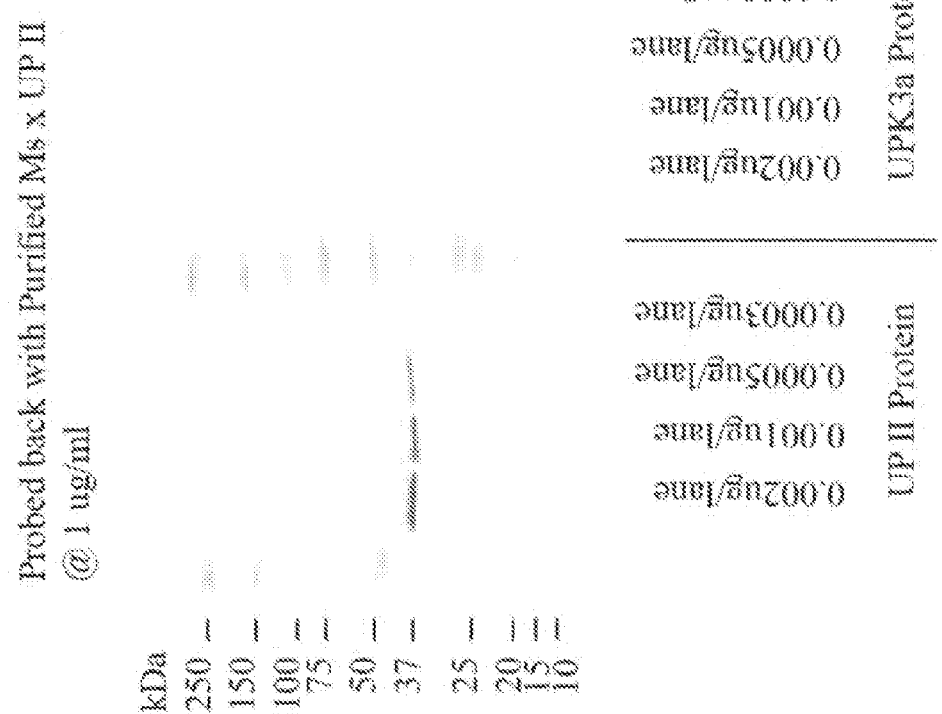

Binding of BC21 to UP II protein may be demonstrated by Western blot (FIG. 9A). The absence of similar binding of BC21 to UP III protein may also be shown by Western blot (FIG. 9A). Conversely, the anti-UP III antibody BC17 may not bind UP II protein, but may recognize UP III protein (FIG. 9B).

In some embodiments of the present invention, anti-UPII antibodies such as the mouse monoclonal anti-UP II antibody BC21 may be suitable for use in many variations of the above protocols and other methods known to those in the art. Specimens stained with BC21 may be archived using a permanent mounting media and a coverslip. The antibody BC21 may also be used in an automated staining instrument, using standard protocols. One can also envision the use of many alternative detection methods (e.g., fluorescence), detection enzymes (e.g., alkaline phosphatase (AP), beta-galactosidase, or the like), and perhaps even chromogens (e.g., 3-amino-9-ethylcarbazole, 5-bromo-4-chloro-3-indolyl phosphate, 3,3',5,5'-tetramethylbenzidine, 5-bromo-4-chloro-3-indolyl-β-D-glucuronide, or the like), generally known to those in the art.

An epitope of an anti-UPII antibodies such as mouse monoclonal anti-UP II antibody, or a portion thereof, may be a useful antigen for the production of new monoclonal antibodies, including production in species other than mouse (e.g. rabbit, goat, horse, chicken, etc.) as one skilled in the art would understand. A monoclonal antibody for Uroplakin III may include but is not limited to a mouse monoclonal antibody, a rabbit monoclonal antibody, a goat monoclonal antibody, a horse monoclonal antibody, a chicken monoclonal antibody, a humanized monoclonal antibody, a chimeric antibody, any combination thereof, or the like. In other embodiments, a polyclonal antibody for Uroplakin III may include but is not limited to rabbit polyclonal antibody, mouse polyclonal antibody, a goat polyclonal antibody, a horse polyclonal antibody, a chicken polyclonal antibody, a humanized polyclonal antibody, any combination thereof, or the like. In yet other embodiments, an antibody may be an isolated antibody.

While the use of anti-UPII antibodies such as BC21 in immunohistochemistry of formalin-fixed paraffin embedded tissues may be described here, its utility in other immunoassays may be readily envisioned and all are included in this application. In particular, it may be well known that many of the same reagents used in IHC of FFPE may also be used in IHC of frozen-tissue sections. Anti-UPII antibodies such as BC21 may also be useful in other immunoassays, including ELISA, perhaps using generally known methods.

In another aspect of the invention, perhaps related to IHC, an anti-UP II antibody may be used in conjunction with one or more additional primary antibodies as part of a cocktail, to perform a "double-stain" procedure (also described as multi-stain or even multiplex). Such "double-stain" procedures may be generally well known in the art; however, the best combinations of primary antibodies for a particular diagnostic application may not be known.

In this method, anti-UPII antibodies such as a mouse monoclonal anti-UP II antibody BC21 could be combined with one or more antibodies in a primary antibody cocktail. At least one of the additional antibodies could be derived from a species other than mouse such as a rabbit antibody or the like. Antibodies may be derived from at least two different species such as but not limited to a mouse host or a rabbit host or the like. Species may include but are not limited to mouse, rabbit, goat, horse, chicken, human, any combination thereof, or the like. The antibodies may be monoclonal or polyclonal. In this manner, the multiple antibodies in the primary antibody cocktail may be differentiated in the subsequent detection and even visualization steps. For example, following incubation of the tissue sample with the primary antibody cocktail, the usual goat anti-mouse antibody conjugated to HRP may be applied perhaps followed by an appropriate chromogen, such as DAB or the like. Subsequently, a second detection step may be performed, using goat anti-rabbit antibody conjugated to AP perhaps followed by an appropriate chromogen, such as Fast Red or the like. In this manner, two or more targets may be identified on the same tissue sample with the resulting two colors. In this specific example, mouse primary antibodies (including BC21) could result in brown (DAB) staining and rabbit primary antibodies could result in red (Fast Red) staining.

The anti-mouse or anti rabbit antibodies comprising the antibody-enzyme conjugates may be derived from a different host species, including, but not limited to mouse, rabbit, chicken, horse, rat, goat, sheep, or the like. A primary antibody may be from a variety of host species, including, but not limited to mouse, rabbit, chicken, horse, rat, goat, sheep, or the like. In embodiments, an antibody may include an antibody-enzyme conjugate and a primary antibody could be obtained from two different host species. Chromogens other than DAB and/or Fast Red may be used as well.

Multiple alternatives to a double-staining method are possible, including but not limited to the use of more than two antibodies, the use of species other than mouse and rabbit, other chromogens and detection systems, a different order of detection steps, and perhaps even modifications resulting in three or more colors (which may require a denaturing step).

Embodiments of the present invention may provide a composition having at least two antibodies or fragments thereof, perhaps as a cocktail, where at least one of the two antibodies or fragments thereof specifically binds to at least Uroplakin II. This may provide a method for detecting at least two different proteins in a biological sample perhaps by contacting a biological sample with a composition comprising at least two antibodies or fragments thereof, where at least one of the at least two antibodies or fragments thereof may bind specifically to at least Uroplakin II, to form an antigen-antibody complex and an antigen-antibody complex may be detected. A composition may have at least one first primary antibody and at least one second primary antibody. A biological sample may include but is not limited to blood, urine, bladder tissue, urothelial tissue, transitional cell tissue, normal tissue, neoplastic tissue, kidney tissue, ovarian tissue, thyroid tissue, endometrial tissue, renal tissue, tonsil tissue, pancreas tissue, colon tissue, lymph node tissue, neoplastic pancreatic tissue, stomach tissue, prostate tissue, lung tissue and breast tissue, or the like.

At least one of the antibodies or fragments thereof may specifically bind to at least Uroplakin II and may even have a positive indication cut-off value of greater than 1% of stained cells. As mentioned herein, a positive indication cut-off value may provide a percentage of stained cells needed to indicate a positive staining result. Other cut-off value may include but are not limited to greater than about 1% of stained cells, greater than about 2% of stained cells, greater than about 3% of stained cells, greater than about 4% of stained cells, greater than about 5% of stained cells, greater than about 6% of stained cells, greater than about 7% of stained cells, greater than about 8% of stained cells, greater than about 9% of stained cells, and perhaps even greater than about 10% of stained cells, or more, or the like.

In embodiments, the present invention may provide a composition with at least two antibodies or fragments thereof which may be capable of providing different visualization results such as different color results. As discussed in other embodiments, below, a composition may provide that at least one other of an at least two antibodies or fragments thereof may bind specifically to GATA-3, p63, Uroplakin III, PAX8, NKX3.1, PSA, any combination thereof, or the like. Antibodies, compositions thereof, perhaps with anti-Uroplakin II antibodies may provide a detection system including but not limited to urothelial carcinoma detection composition, renal cell carcinoma detection composition, prostate/prostatic carcinoma detection composition, any combination thereof, or the like.

In some embodiments, a single color stain may be used for a primary antibody cocktail. In one example, if the primary antibody cocktail is comprised of antibodies all derived from the same host species, then a single antibody enzyme conjugate may be used to stain for the presence of all of the antibodies with a single color. The presence or absence of each antibody may be determined based on cellular localization, or perhaps such determination is not necessary and the staining may be interpreted effectively without identifying the presence or absence of each individual antibody.

Certain steps of an IHC procedure may be performed sequentially or simultaneously, perhaps by using a cocktail of reagents, as known to those skilled in the art. For example, antibodies described in a primary antibody cocktail may alternatively be applied in sequential steps of one or more antibodies. Similarly, detection reagents may be applied simultaneously in reagent cocktail or separate reagents in sequential steps.

In some embodiments, a first primary antibody may be applied, followed by a first antibody-enzyme conjugate and first chromogen, and then a denaturing step, before proceeding to application of a second primary antibody, followed by a second antibody-enzyme conjugate and a second chromogen. In this manner, a double-stain of two different colors may be achieved using primary antibodies derived from the same species.

Antibodies that may be useful for diagnosis when combined with an anti-UPII antibody such as a mouse monoclonal anti-UP II antibody BC21 in a primary antibody cocktail for use in multi-stain procedures may include:

TABLE 5

| Antibody Cocktail | Utility |
| --- | --- |
| UPII + UPIII | Urothelial marker of enhanced sensitivity |
| UPII + GATA3 | Urothelial marker of enhanced sensitivity |
| UPII + UPIII + GATA3 | Urothelial marker of enhanced sensitivity |
| UPII + PAX8 | Differential marker of bladder and kidney |
| UPII + PAX8 + PSA | Differential marker of bladder, kidney and prostate |
| UPII + NKX3.1 | Differential marker of bladder and prostate |
| UPII + PAX8 + NKX3.1 | Differential marker of bladder, kidney and prostate |
| UPII + p63 | Urothelial marker of enhanced sensitivity and differential marker of bladder and prostate and differential marker of bladder and non-bladder squamous cell carcinoma |
| UPII + GATA-3 and/or p63 + PAX8 + PSA and/or NKX3.1 | Differential marker of bladder, kidney, and prostate cancer |
| UPII + p40 | Urothelial marker of enhanced sensitivity and differential marker of bladder and prostate and differential marker of bladder and non-bladder squamous cell carcinoma |

An anti-UPII antibody such as a mouse monoclonal anti-UP II antibody BC21 may be specific for detection of UP II and may be useful in immunohistochemical procedures for diagnosis of several types of cancers in human tissue samples. In particular, anti-UP II antibody such as BC21 has advantages over anti-UP III antibody BC17, including but not limited to greater sensitivity.

Expression levels of UP II protein may be a prognostic marker of patient outcomes in cases of bladder cancer. Determination of UP II expression, using an antibody such as BC21, may aid in identifying patients more likely to experience a positive outcome (e.g. longer survival time, longer time to disease progression, reduced tumor size, or the like), a positive or good prognosis, or those patients more likely to experience a negative outcome (e.g. shorter survival time, shorter time to disease progression, or the like), a negative or poor prognosis. Determination of UP II expression, using an antibody such as BC21, may also aid in predicting patient response to a particular therapeutic treatment. For example, the level of UPII expression may aid in determining the likelihood that a patient could benefit from a particular pharmaceutical agent, including antibody based therapeutics. Conversely, UP II expression may aid in determining the likelihood that a patient may not benefit from a particular therapeutic treatment.

Alternative embodiments of antibodies that may be useful for diagnosis when combined with an UPII antibody such as a mouse monoclonal UPII antibody BC21 in a primary antibody cocktail for use in multi-stain procedures can include:

TABLE 6

Figure 10:
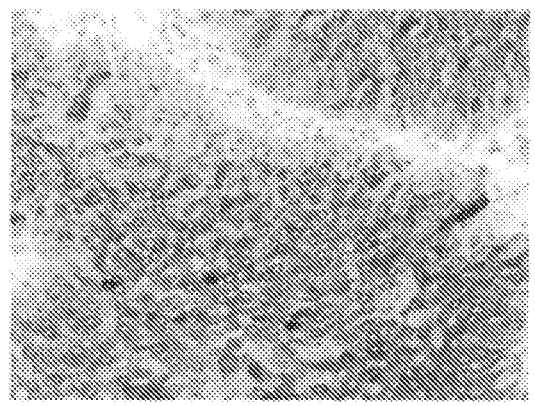
FIG. 10 shows an example of a cocktail of UPII+UPIII staining urothelial carcinoma. Staining of UPII (brown) is membranous and cytoplasmic.
Figure 11:
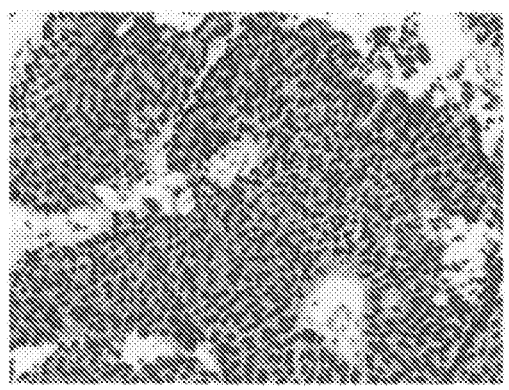
FIG. 11 shows an example of a cocktail of UPII+GATA3 staining urothelial carcinoma. Staining of UPII (red) is membranous and cytoplasmic. Staining of GATA3 (brown) is nuclear.
Figure 12:
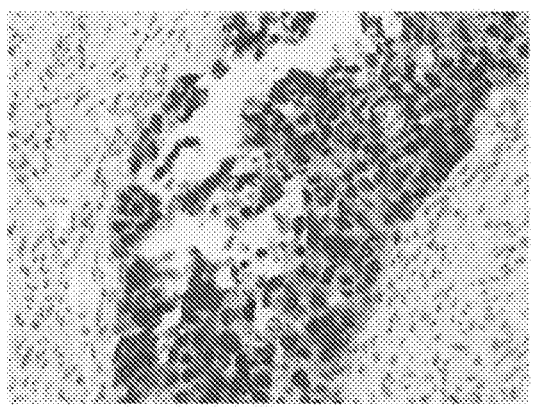
FIG. 12 shows an example of a cocktail of UPII+GATA3 staining urothelial carcinoma. Staining of UPII (red) is membranous and cytoplasmic. Staining of GATA3 (brown) is nuclear.
Figure 13:
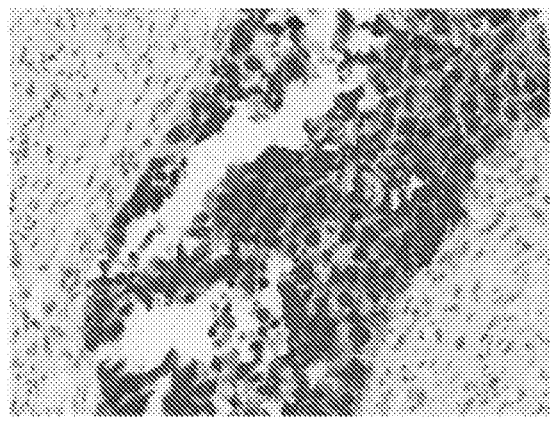
FIG. 13 shows an example of a cocktail of UPII+UPIII+GATA3 staining urothelial carcinoma. Staining of UPII and UPIII (red) is membranous and cytoplasmic. Staining of GATA3 (brown) is nuclear.

| Antibody Combination (Host Species, cellular localization, stain color*) | Possible Diagnostic Utility | Detection System used in example and Figure No. |
| --- | --- | --- |
| UPIII (Mouse, Membrane & cytoplasmic, brown) UPII (Mouse, Membrane & cytoplasmic, brown) | UPII and/or UPIII staining may be observed in urothelial carcinoma. | Goat anti-mouse HRP FIG. 10 |
| UPII (Mouse, Membrane & cytoplasmic, red) GATA3 (Rabbit, nuclear, brown) | UPII and/or GATA3 staining may be observed in urothelial carcinoma. | DS#1 FIGS. 11, 12 |
| UPII (Mouse, Membrane & cytoplasmic, red) UPIII (Mouse, Membrane & cytoplasmic, red) GATA3 (Rabbit, nuclear, brown) | UPII and/or UPIII and/or GATA3 staining may be observed in urothelial carcinoma. | DS#1 FIG. 13 |
| UPII (Mouse, Membrane & cytoplasmic, red) PAX8 (Rabbit, nuclear, brown) | UPII staining may be observed in urothelial carcinoma. PAX8 staining may be observed in renal cell carcinoma. | DS#1 FIGS. 14, 15, 16, 17 |
| UPII (Mouse, Membrane & cytoplasmic, red) PAX8 (Rabbit, nuclear, brown) PSA (Rabbit, cytoplasmic, brown) | UPII staining may be observed in urothelial carcinoma. PAX8 staining may be observed in renal cell carcinoma. PSA staining may be observed in prostatic carcinoma. | DS#1 FIGS. 18, 19, 20 |
| UPII (Mouse, Membrane & cytoplasmic, brown) PAX8 (Rabbit, nuclear, red) PSA (Rabbit, cytoplasmic, red) | UPII staining may be observed in urothelial carcinoma. PAX8 staining may be observed in renal cell carcinoma. PSA staining may be observed in prostatic carcinoma. | DS#2 FIGS. 21, 22, 23 |
| UPII (Mouse, Membrane & cytoplasmic, brown) NKX3.1 (Rabbit, nuclear, red) | UPII staining may be observed in urothelial carcinoma. NKX3.1 staining may be observed in prostatic carcinoma. | DS#2 FIGS. 24, 25 |
| UPII (Mouse, Membrane & cytoplasmic, brown) PAX8 (Mouse, nuclear, brown) | UPII staining may be observed in urothelial carcinoma. PAX8 staining may be observed in renal cell carcinoma. | DS#2 FIGS. 26, 27, 28 |

TABLE 6-continued

Figure 29:
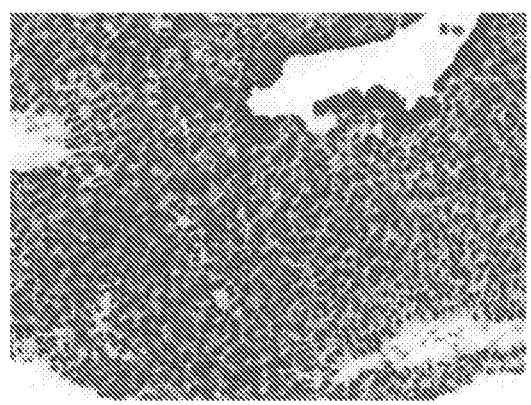
FIG. 29 shows an example of a cocktail of UPII+p63 staining urothelial carcinoma. Staining of p63 (brown) is nuclear. Staining of UPII (red) is membranous and cytoplasmic.
Figure 30:
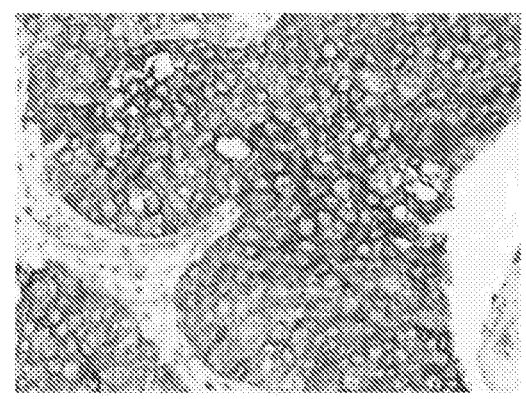
FIG. 30 shows an example of a cocktail of UPII+p63 staining urothelial carcinoma. Staining of UPII (brown) is membranous and cytoplasmic. Staining of p63 (nuclear, brown) may be reduced or perhaps absent in this sample.
Figure 31:
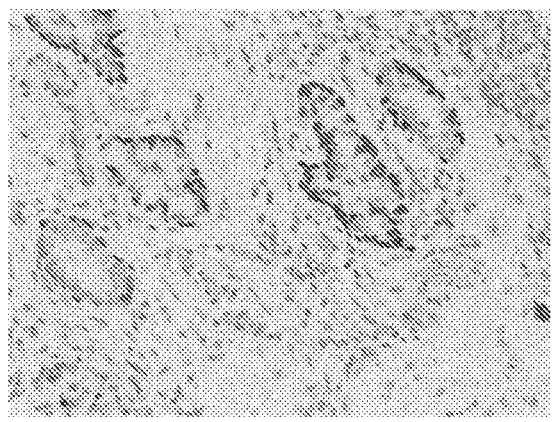
FIG. 31 shows an example of a cocktail of UPII+p63 staining prostatic intraepithelial neoplasia (PIN). Staining of p63 (brown) is nuclear. Staining of UPII (membranous and cytoplasmic, brown) may be reduced or perhaps absent in this sample.
Figure 32:
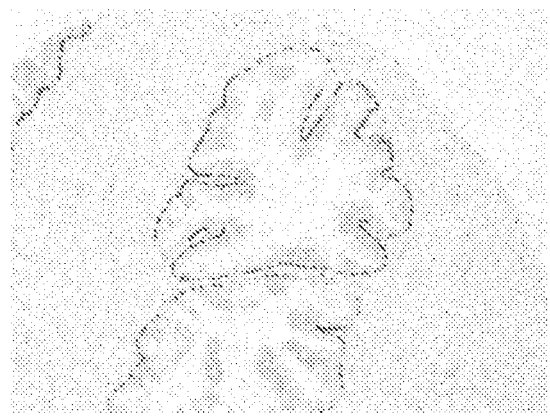
FIG. 32 shows an example of a cocktail of UPII+p63 staining normal prostate. Staining of p63 (brown) is nuclear. Staining of UPII (membranous and cytoplasmic, brown) may be reduced or perhaps absent in this sample.
Figure 33:
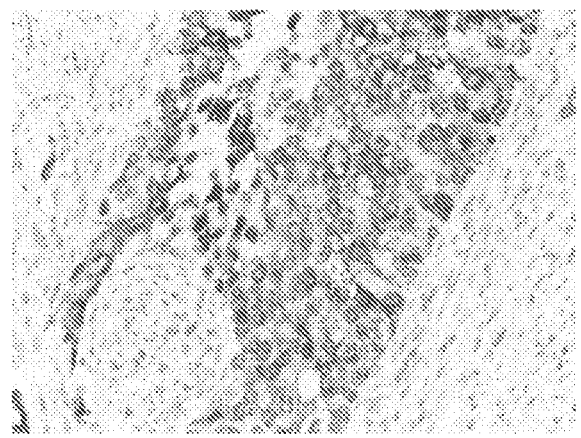
FIG. 33 shows an example of a cocktail of UPII+p63 staining urothelial carcinoma. Staining of p40 (brown) is nuclear. Staining of UPII (red) is membranous and cytoplasmic.

| Antibody Combination (Host Species, cellular localization, stain color*) | Possible Diagnostic Utility | Detection System used in example and Figure No. |
|---|---|---|
| NKX3.1 (Rabbit, nuclear, red) | NKX3.1 staining may be observed in prostatic carcinoma. | |
| UPII (Mouse, Membrane & cytoplasmic, red) | UPII staining may be observed in urothelial carcinoma. | Goat anti-mouse HRP and Goat anti-mouse AP FIG. 29 |
| p63 (Mouse, nuclear, brown) | p63 staining may be observed in urothelial carcinoma. | |
| UPII (Mouse, Membrane & cytoplasmic, brown) | UPII staining may be observed in urothelial carcinoma. | Goat anti-mouse HRP FIGS. 30, 31, 32 |
| p63 (Mouse, nuclear, brown) | p63 staining may be observed in normal prostate or PIN. | |
| UPII (Mouse, Membrane & cytoplasmic, red) | UPII staining may be observed in urothelial carcinoma. | Goat anti-mouse HRP and Goat anti-mouse AP FIG. 33 |
| p40 (Mouse, nuclear, brown) | p40 staining may be observed in urothelial carcinoma. | |

*The listed color of each stain may be a result of a detection system that may include an anti-mouse antibody perhaps conjugated to HRP and even an anti-mouse antibody perhaps conjugated to AP, perhaps even with DAB and Fast Red as chromogens, which may result in brown staining for mouse antibodies and red staining for rabbit antibodies (referred to as DS#2). Alternatively, the detection system may include an anti-mouse antibody perhaps conjugated to AP and even an anti-rabbit antibody perhaps conjugated to HRP, perhaps even with DAB and Fast Red as chromogens, which may result in red staining for mouse antibodies and brown staining for rabbit antibodies (referred to as DS#1). In some instances, two colors may not be necessary because the antigens may be distinguished by cellular localization of staining, or perhaps it is not diagnostically significant to determine which antigen is staining. Other color combinations may be obtained using other detection systems or chromogens and all are meant to be included in this disclosure.

The non-limiting examples of various cocktails listed in Table 6 are examples only and is not intended to suggest that every case of a particular cancer could produce the same result. For example, not all cases of urothelial carcinoma could be positive for UPII and/or GATA3. Additionally, not all cases of renal cell carcinoma could be positive for PAX8, and the like. Each marker may be reduced or may even be absent in other cases.

In some embodiments, combining UPII with another antibody that stains urothelial tissue, such as UPIII, may be useful, perhaps increasing sensitivity compared to staining with each of the antibodies individually. FIG. 10 shows an example of a cocktail of UPIII+UPII staining a specimen of urothelial carcinoma. In some cases, UPII staining may be observed, when perhaps UPIII staining is reduced or absent. In other cases, UPIII staining may be observed, when perhaps UPII staining is reduced or absent.

A cocktail of UPII+GATA3 may also provide increased sensitivity for urothelial carcinoma. A specimen of urothelial carcinoma stained with a cocktail of UPII+GATA3 is shown in FIG. 11. In some cases, UPII staining may be observed, when perhaps GATA3 staining is reduced or absent. In other cases, GATA3 staining may be observed, when perhaps UPII staining is reduced or absent.

Combining multiple markers of urothelial carcinoma may further enhance sensitivity. A specimen stained with a cocktail of UPII+GATA3 is shown in FIG. 12. The same specimen stained with a cocktail of UPII+UPIII+GATA3 is shown in FIG. 13. Perhaps more staining is observed with the UPII+UPIII+GATA3 cocktail, which may result in improved sensitivity.

Figure 14:
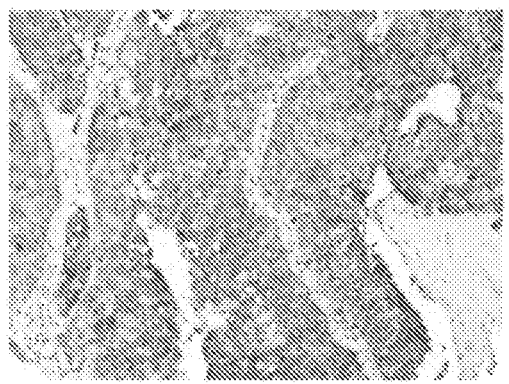
FIG. 14 shows an example of a cocktail of UPII+PAX8 staining urothelial carcinoma. Staining of UPII (red) is membranous and cytoplasmic. Staining of PAX8 (nuclear, brown) may be reduced or perhaps absent in this sample.
Figure 15:
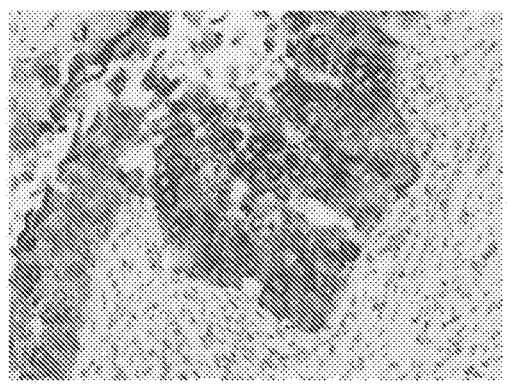
FIG. 15 shows an example of a cocktail of UPII+PAX8 staining urothelial carcinoma. Staining of UPII (red) is membranous and cytoplasmic. Staining of PAX8 (nuclear, brown) may be reduced or perhaps absent in this sample.
Figure 16:
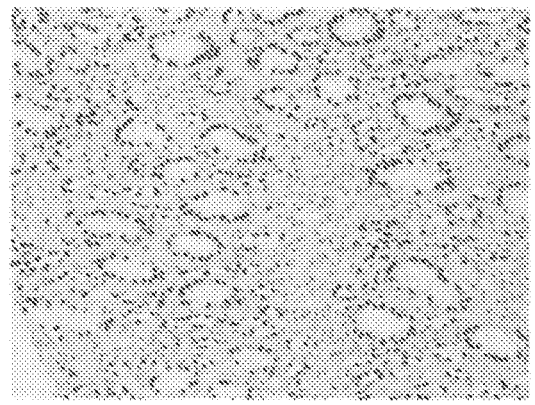
FIG. 16 shows an example of a cocktail of UPII+PAX8 staining renal cell carcinoma. Staining of PAX8 (brown) is nuclear. Staining of UPII (membranous and cytoplasmic, red) may be reduced or perhaps absent in this sample.
Figure 17:
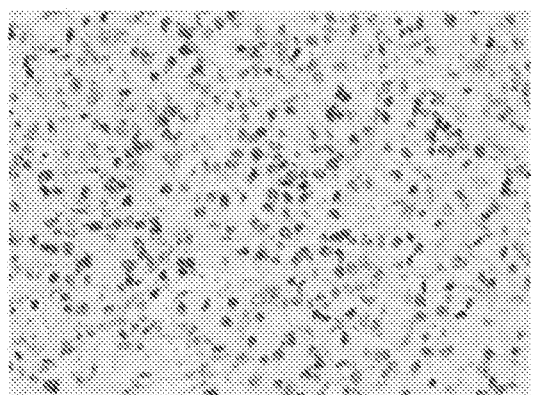
FIG. 17 shows an example of a cocktail of UPII+PAX8 staining renal cell carcinoma. Staining of PAX8 (brown) is nuclear. Staining of UPII (membranous and cytoplasmic, red) may be reduced or perhaps absent in this sample.

Combining UPII+PAX8 may be useful for differentiating urothelial carcinoma and renal cell carcinoma. UPII may stain urothelial carcinoma, which is not stained by PAX8 (FIGS. 14 and 15). In contrast, renal cell carcinoma may be stained by PAX8, but perhaps not by UPII (FIGS. 16 and 17).

Figure 18:
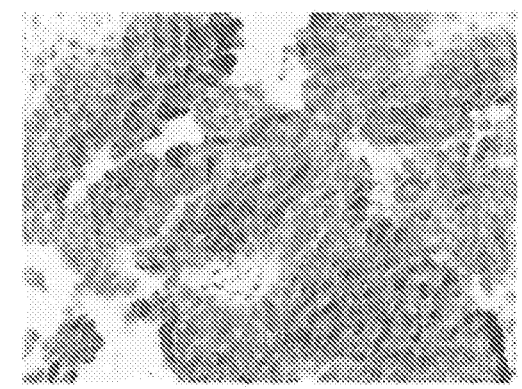
FIG. 18 shows an example of a cocktail of UPII+PAX8+PSA staining urothelial carcinoma. Staining of UPII (red) is membranous and cytoplasmic. Staining of PAX8 and PSA (nuclear and cytoplasmic, respectively; brown) may be reduced or perhaps absent in this sample.
Figure 19:
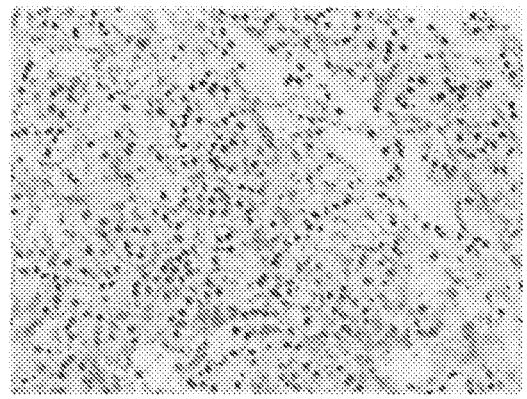
FIG. 19 shows an example of a cocktail of UPII+PAX8+PSA staining renal cell carcinoma. Staining of PAX8 (brown) is nuclear. Staining of UPII (membranous and cytoplasmic, red) and PSA (cytoplasmic, brown) may be reduced or perhaps absent in this sample.
Figure 20:
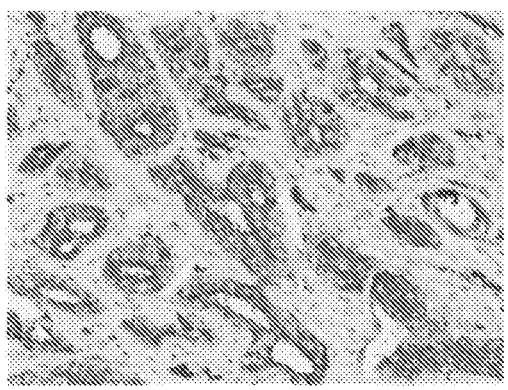
FIG. 20 shows an example of a cocktail of UPII+PAX8+PSA staining prostate cancer. Staining of PSA (brown) is cytoplasmic. Staining of UPII (membranous and cytoplasmic, red) and PAX8 (nuclear, brown) may be reduced or perhaps absent in this sample.
Figure 21:
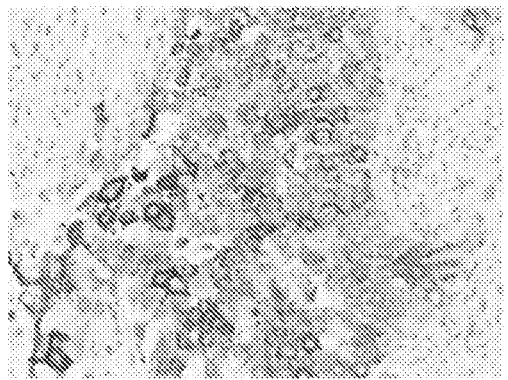
FIG. 21 shows an example of a cocktail of UPII+PAX8+PSA staining urothelial carcinoma. Staining of UPII (brown) is membranous and cytoplasmic. Staining of PAX8 and PSA (nuclear and cytoplasmic, respectively; red) may be reduced or perhaps absent in this sample.
Figure 22:
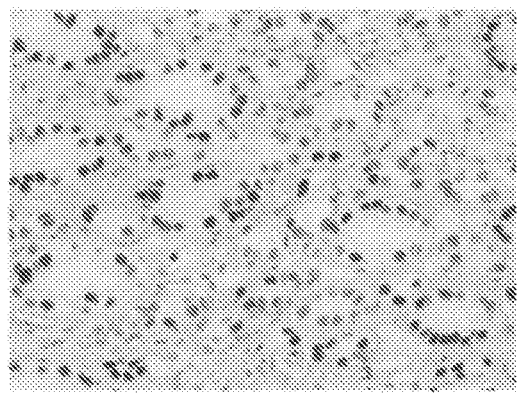
FIG. 22 shows an example of a cocktail of UPII+PAX8+PSA staining renal cell carcinoma. Staining of PAX8 (red) is nuclear. Staining of UPII (membranous and cytoplasmic, brown) and PSA (cytoplasmic, red) may be reduced or perhaps absent in this sample.
Figure 23:
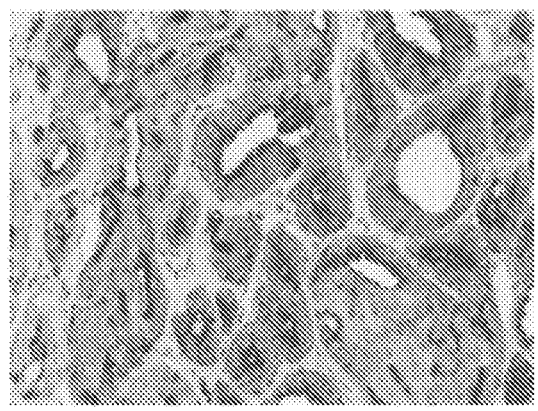
FIG. 23 shows an example of a cocktail of UPII+PAX8+PSA staining prostate cancer. Staining of PSA (red) is cytoplasmic. Staining of UPII (membranous and cytoplasmic, brown) and PAX8 (nuclear, red) may be reduced or perhaps absent in this sample.

Combining UPII+PAX8+PSA may be useful for differentiating urothelial carcinoma renal cell carcinoma, and prostate carcinoma. UPII may stain urothelial carcinoma, which is not stained by PAX8 or PSA (FIGS. 18 and 21). In contrast, renal cell carcinoma may be stained by PAX8, but perhaps not by UPII or PSA (FIGS. 19 and 22). Additionally, prostate carcinoma may be stained by PSA, but perhaps not by UPII or PAX8 (FIGS. 20 and 23).

Figure 24:
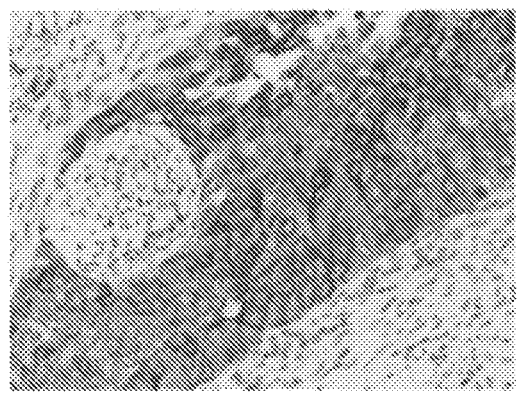
FIG. 24 shows an example of a cocktail of UPII+NKX3.1 staining urothelial carcinoma. Staining of UPII (red) is membranous and cytoplasmic. Staining of NKX3.1 (nuclear, brown) may be reduced or perhaps absent in this sample.
Figure 25:
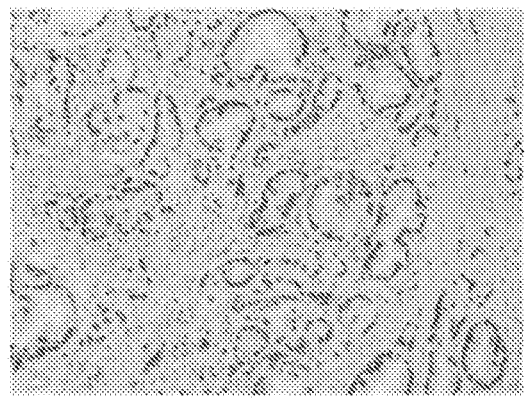
FIG. 25 shows an example of a cocktail of UPII+NKX3.1 staining prostate cancer. Staining of NKX3.1 (brown) is nuclear. Staining of UPII (membranous and cytoplasmic, red) may be reduced or perhaps absent in this sample.

Combining UPII+NKX3.1 may be useful for differentiating urothelial carcinoma and prostate carcinoma. UPII may stain urothelial carcinoma, which is not stained by NKX3.1 (FIG. 24). In contrast, prostate carcinoma may be stained by NKX3.1, but perhaps not by UPII (FIG. 25).

Figure 26:
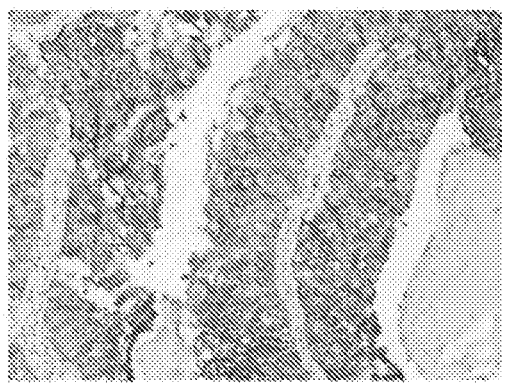
FIG. 26 shows an example of a cocktail of UPII+PAX8+NKX3.1 staining urothelial carcinoma. Staining of UPII (brown) is membranous and cytoplasmic. Staining of PAX8 (nuclear, brown) and NKX3.1 (nuclear, red) may be reduced or perhaps absent in this sample.
Figure 27:
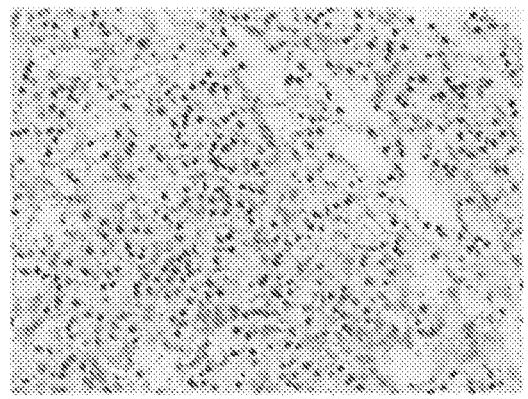
FIG. 27 shows an example of a cocktail of UPII+PAX8+NKX3.1 staining renal cell carcinoma. Staining of PAX8 (brown) is nuclear. Staining of UPII (membranous and cytoplasmic, brown) and NKX3.1 (nuclear, red) may be reduced or perhaps absent in this sample.
Figure 28:
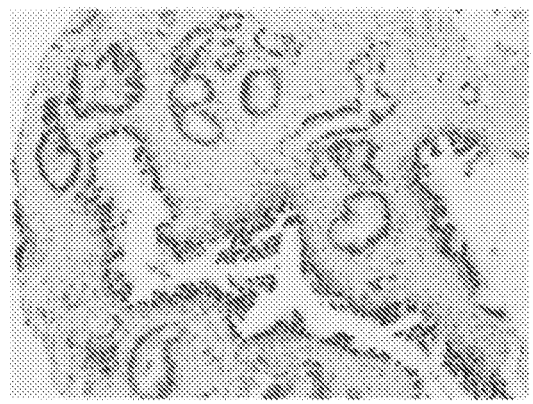
FIG. 28 shows an example of a cocktail of UPII+PAX8+NKX3.1 staining prostate cancer. Staining of NKX3.1 (red) is nuclear. Staining of UPII (membranous and cytoplasmic, brown) and PAX8 (nuclear, brown) may be reduced or perhaps absent in this sample.

Combining UPII+PAX8+NKX3.1 may be useful for differentiating urothelial carcinoma renal cell carcinoma, and prostate carcinoma. UPII may stain urothelial carcinoma, which is not stained by PAX8 or NKX3.1 (FIG. 26). In contrast, renal cell carcinoma may be stained by PAX8, but perhaps not by UPII or NKX3.1 (FIG. 27). Additionally, prostate carcinoma may be stained by NKX3.1, but perhaps not by UPII or PAX8 (FIG. 28).

A cocktail of UPII+p63 may also provide increased sensitivity for urothelial carcinoma. A specimen of urothelial carcinoma stained with a cocktail of UPII+p63 is shown in FIGS. 29 and 30. Normal prostate, or perhaps prostatic intraepithelial neoplasia (PIN) may be stained by p63, but perhaps not by UPII (FIGS. 31 and 32).

A cocktail of UPII+p40 may also provide increased sensitivity for urothelial carcinoma. A specimen of urothelial carcinoma stained with a cocktail of UPII+p40 is shown in FIG. 33.

Figure 34:
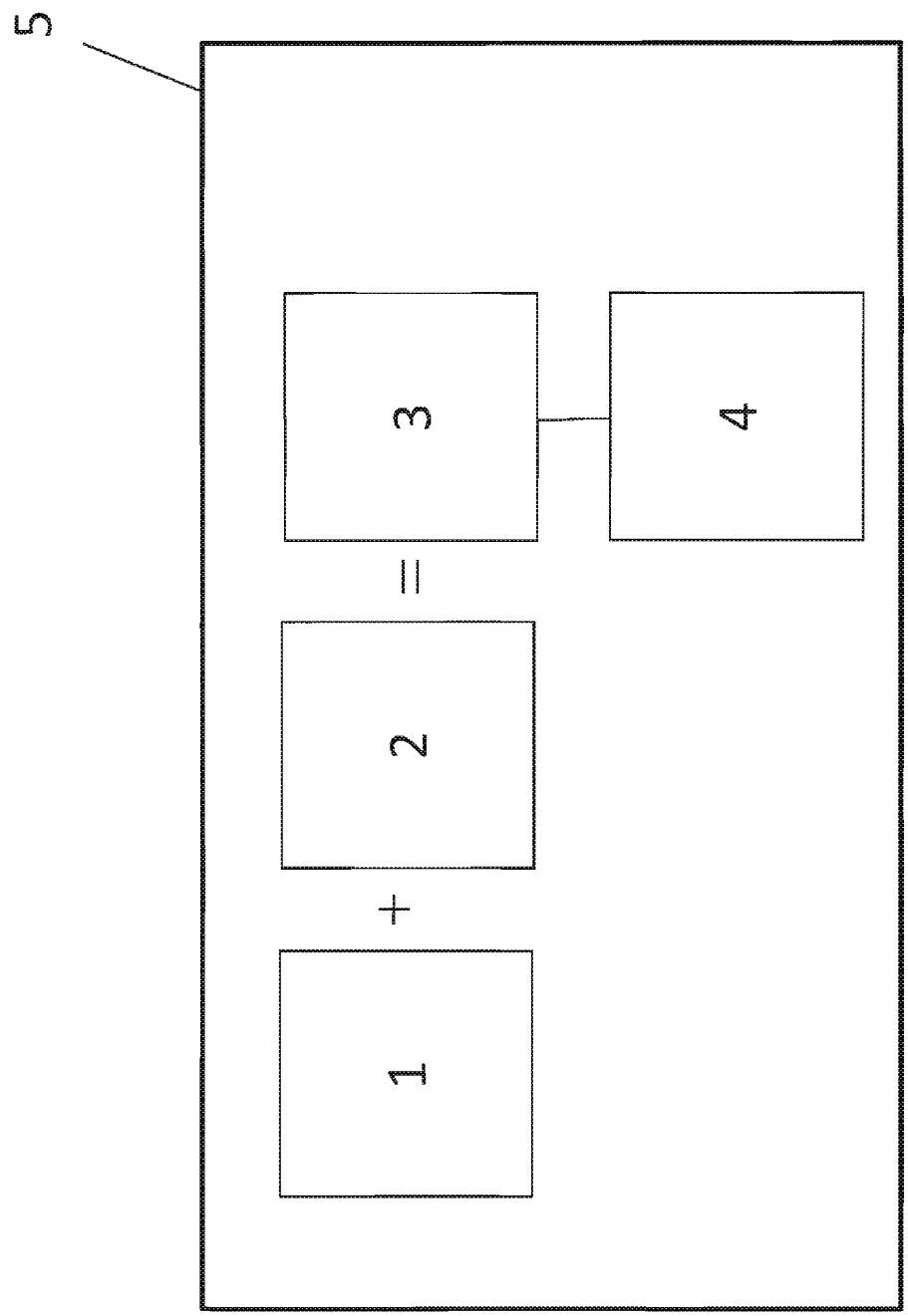
FIG. 34 shows an example of a schematic summary of a kit in accordance with various embodiments of the present invention.

FIG. 34 shows a schematic summary of various embodiments of the present invention including a kit (5) which may provide an antibody, fragment thereof, portion thereof, in a composition or even in a cocktail, perhaps even provided from a hybridoma, the antibody (1) or the like may be contacted with a biological sample (2) to form at least one antibody-antigen complex (3) which may then be detected with a detector (4).

Figure 35:
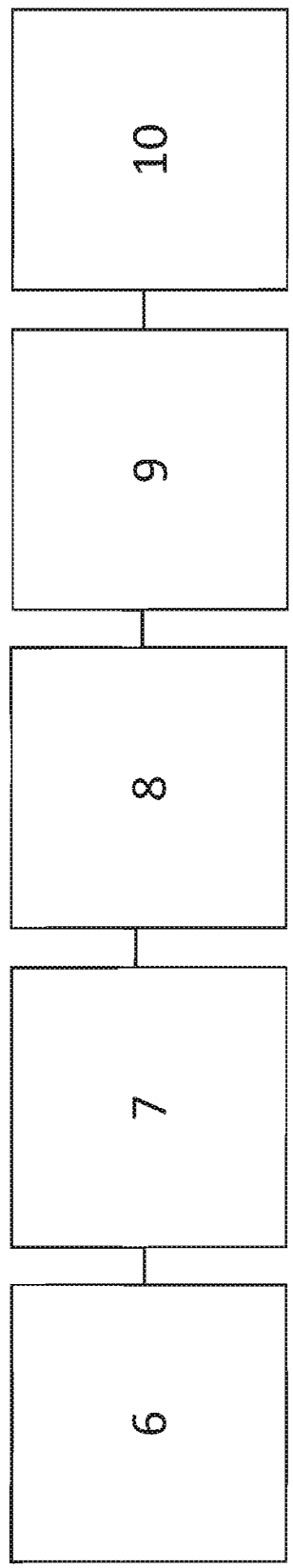
FIG. 35 shows an example of a schematic summary of an immunoassay method in accordance with various embodiments of the present invention.
Figure 36:
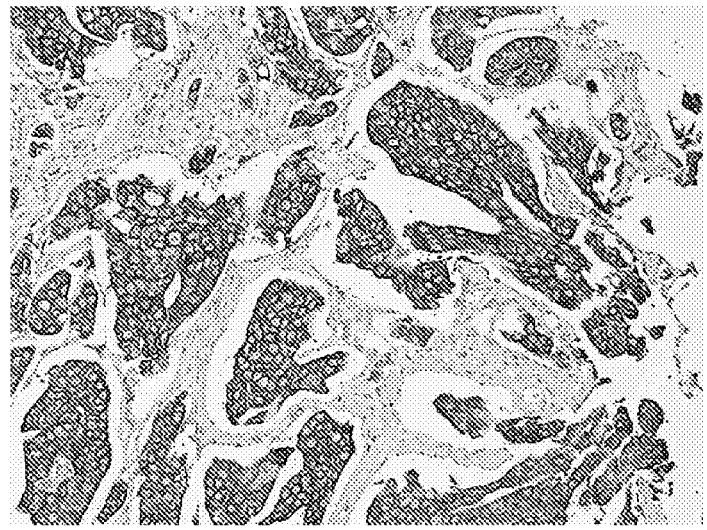
FIG. 36 is a color version of FIG. 1 showing an example of anti-UP II antibody [BC21] staining on bladder TCC tissue (grade 3).
Figure 37:
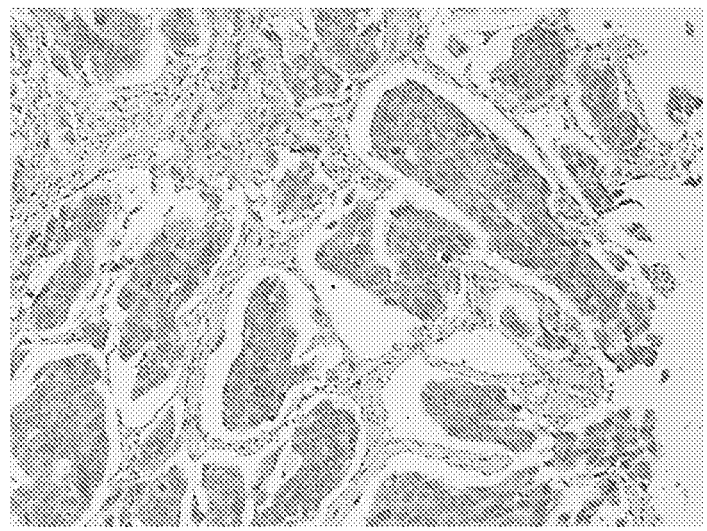
FIG. 37 is a color version of FIG. 2 showing an example of anti-UP III antibody [BC17] staining on a serial section of the same bladder TCC tissue of FIG. 36.
Figure 38:
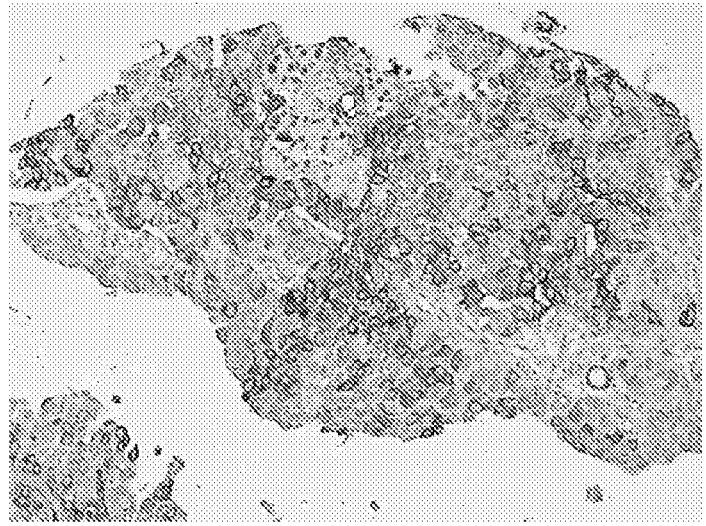
FIG. 38 is a color version of FIG. 3 showing an example of anti-UP II antibody [BC21] staining on bladder TCC tissue (grade 2).
Figure 39:
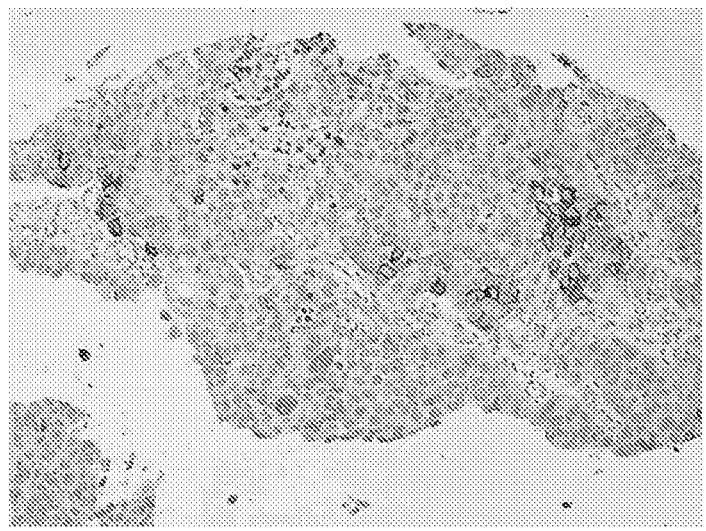
FIG. 39 is a color version of FIG. 4 showing an example of anti-UP III antibody [BC17] staining on a serial section of the same bladder TCC tissue of FIG. 38.
Figure 40:
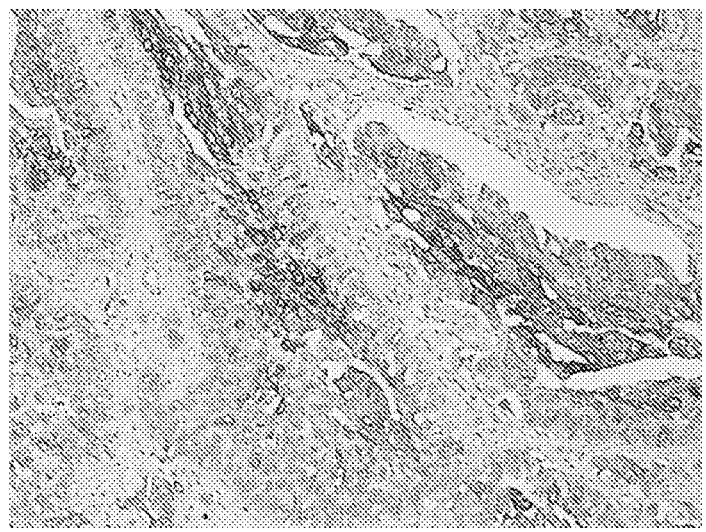
FIG. 40 is a color version of FIG. 5 showing an example of anti-UP II antibody [BC21] staining on bladder TCC tissue (grade 3).
Figure 41:
FIG. 41 is a color version of FIG. 6 showing an example of anti-UP III antibody [BC17] staining on a serial section of the same bladder TCC tissue of FIG. 40.
Figure 42:
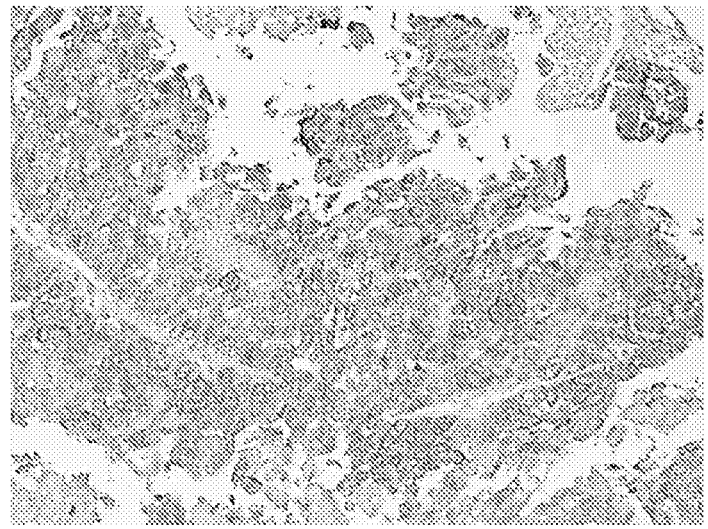
FIG. 42 is a color version of FIG. 7 showing an example of anti-UP II antibody [BC21] staining on bladder TCC tissue (grade 3).
Figure 43:
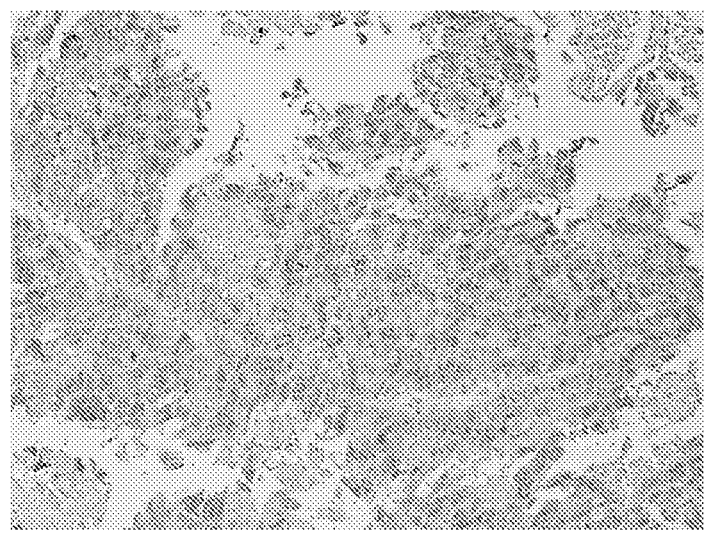
FIG. 43 is a color version of FIG. 8 showing an example of anti-UP III antibody [BC17] staining on a serial section of the same bladder TCC tissue of FIG. 42.
Figures 44A, 44B:
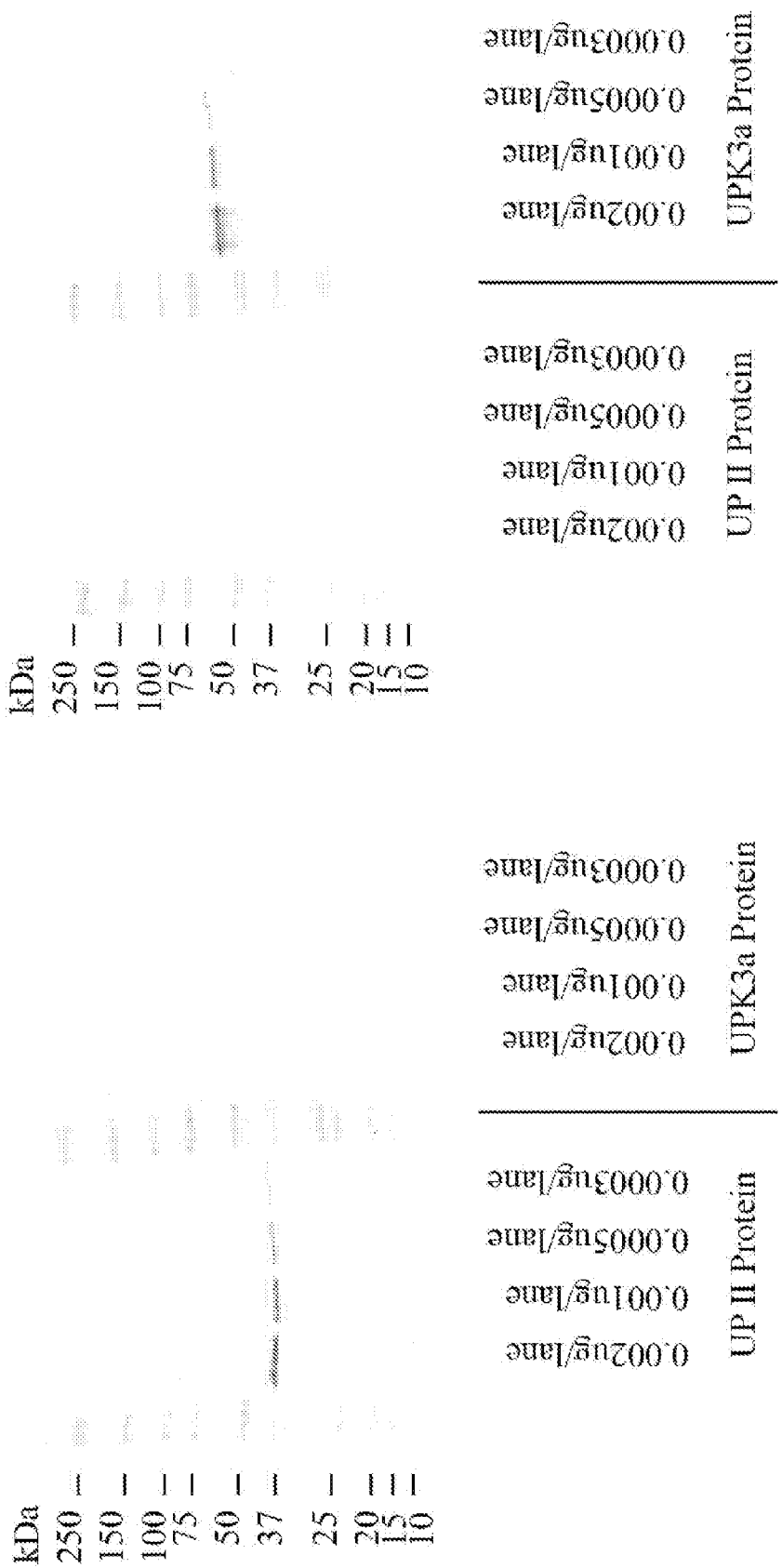
FIGS. 44A and 44B is a color version of FIGS. 9A and 9B showing the cross-reactivity of BC21 and BC17 antibodies with Uroplakin II protein and Uroplakin III protein by Western blot.
Figure 45:
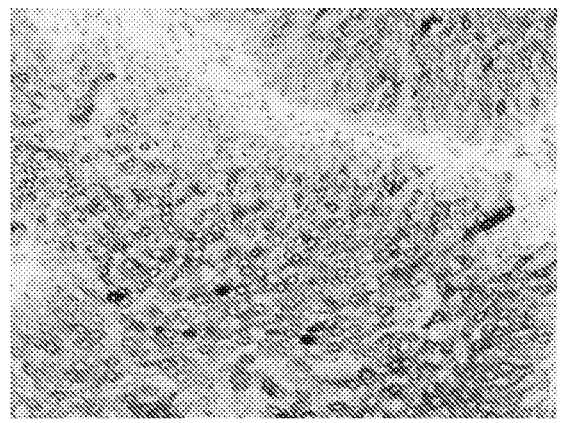
FIG. 45 is a color version of FIG. 10 showing an example of a cocktail of UPII+UPIII staining urothelial carcinoma. Staining of UPII (brown) is membranous and cytoplasmic.
Figure 46:
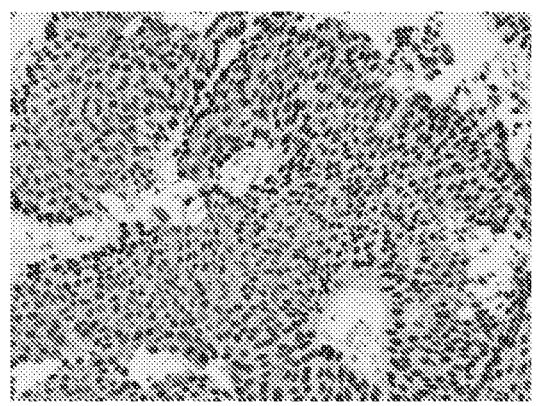
FIG. 46 is a color version of FIG. 11 showing an example of a cocktail of UPII+GATA3 staining urothelial carcinoma. Staining of UPII (red) is membranous and cytoplasmic. Staining of GATA3 (brown) is nuclear.
Figure 47:
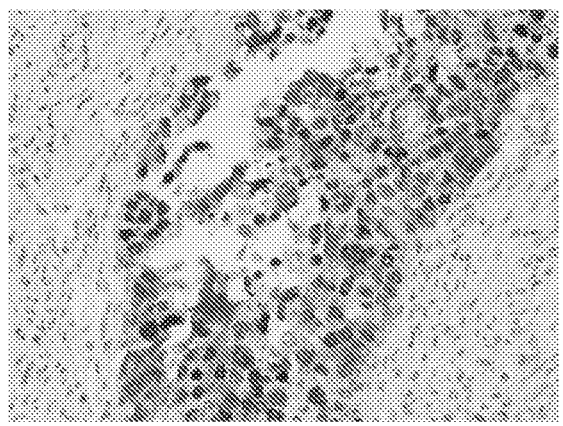
FIG. 47 is a color version of FIG. 12 showing an example of a cocktail of UPII+GATA3 staining urothelial carcinoma. Staining of UPII (red) is membranous and cytoplasmic. Staining of GATA3 (brown) is nuclear.
Figure 48:
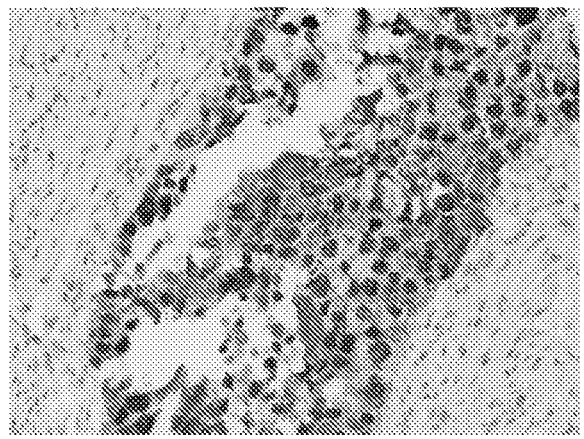
FIG. 48 is a color version of FIG. 13 showing an example of a cocktail of UPII+UPIII+GATA3 staining urothelial carcinoma. Staining of UPII and UPIII (red) is membranous and cytoplasmic. Staining of GATA3 (brown) is nuclear.
Figure 49:
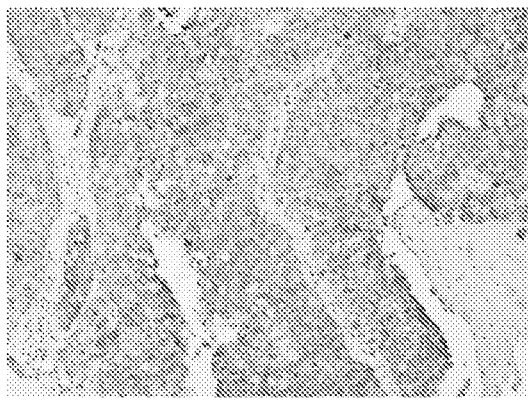
FIG. 49 is a color version of FIG. 14 showing an example of a cocktail of UPII+PAX8 staining urothelial carcinoma. Staining of UPII (red) is membranous and cytoplasmic. Staining of PAX8 (nuclear, brown) may be reduced or perhaps absent in this sample.
Figure 50:
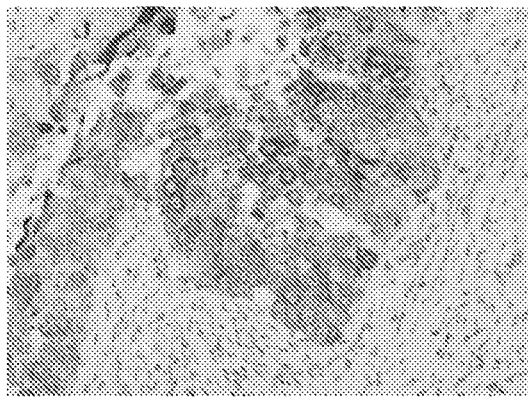
FIG. 50 is a color version of FIG. 15 showing an example of a cocktail of UPII+PAX8 staining urothelial carcinoma. Staining of UPII (red) is membranous and cytoplasmic. Staining of PAX8 (nuclear, brown) may be reduced or perhaps absent in this sample.
Figure 51:
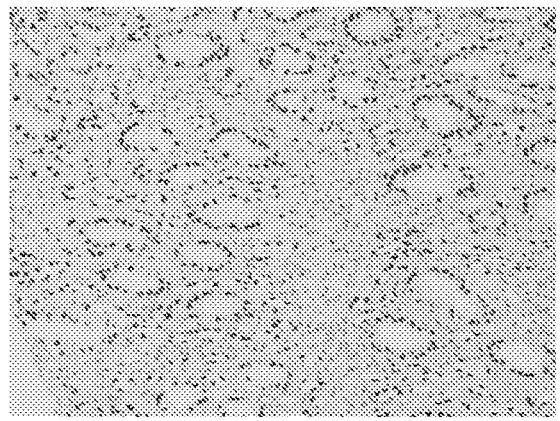
FIG. 51 is a color version of FIG. 16 showing an example of a cocktail of UPII+PAX8 staining renal cell carcinoma. Staining of PAX8 (brown) is nuclear. Staining of UPII (membranous and cytoplasmic, red) may be reduced or perhaps absent in this sample.
Figure 52:
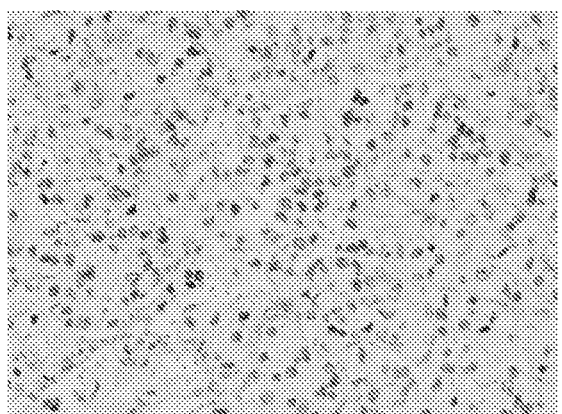
FIG. 52 is a color version of FIG. 17 showing an example of a cocktail of UPII+PAX8 staining renal cell carcinoma. Staining of PAX8 (brown) is nuclear. Staining of UPII (membranous and cytoplasmic, red) may be reduced or perhaps absent in this sample.
Figure 53:
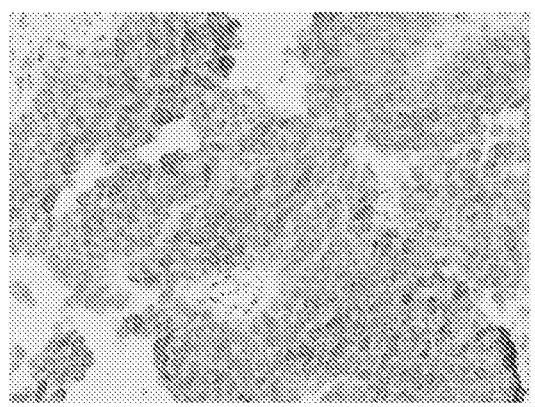
FIG. 53 is a color version of FIG. 18 showing an example of a cocktail of UPII+PAX8+PSA staining urothelial carcinoma. Staining of UPII (red) is membranous and cytoplasmic. Staining of PAX8 and PSA (nuclear and cytoplasmic, respectively; brown) may be reduced or perhaps absent in this sample.
Figure 54:
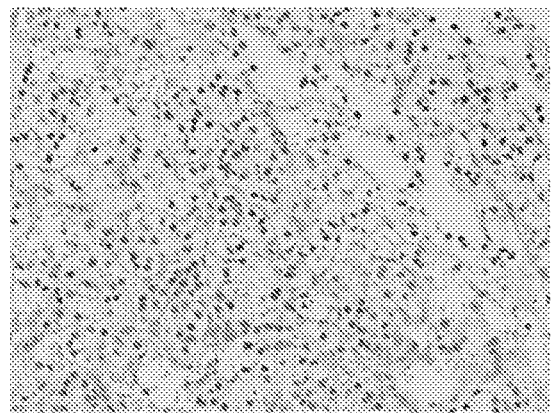
FIG. 54 is a color version of FIG. 19 showing an example of a cocktail of UPII+PAX8+PSA staining renal cell carcinoma. Staining of PAX8 (brown) is nuclear. Staining of UPII (membranous and cytoplasmic, red) and PSA (cytoplasmic, brown) may be reduced or perhaps absent in this sample.
Figure 55:
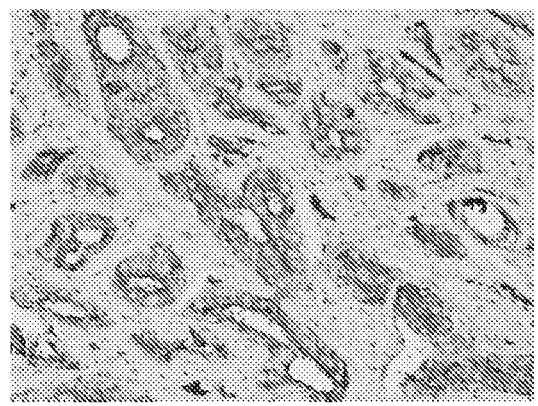
FIG. 55 is a color version of FIG. 20 showing an example of a cocktail of UPII+PAX8+PSA staining prostate cancer. Staining of PSA (brown) is cytoplasmic. Staining of UPII (membranous and cytoplasmic, red) and PAX8 (nuclear, brown) may be reduced or perhaps absent in this sample.
Figure 56:
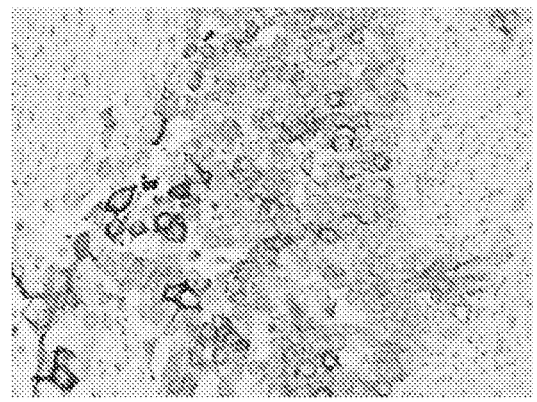
FIG. 56 is a color version of FIG. 21 showing an example of a cocktail of UPII+PAX8+PSA staining urothelial carcinoma. Staining of UPII (brown) is membranous and cytoplasmic. Staining of PAX8 and PSA (nuclear and cytoplasmic, respectively; red) may be reduced or perhaps absent in this sample.
Figure 57:
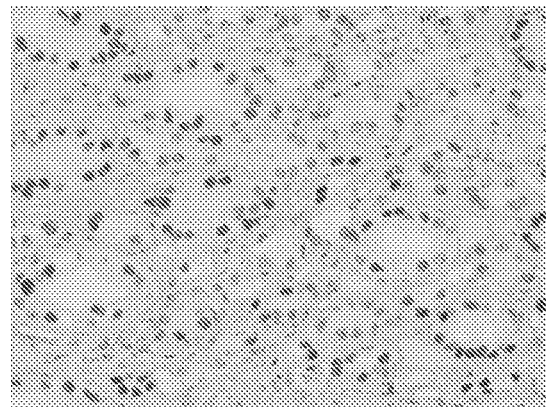
FIG. 57 is a color version of FIG. 22 showing an example of a cocktail of UPII+PAX8+PSA staining renal cell carcinoma. Staining of PAX8 (red) is nuclear. Staining of UPII (membranous and cytoplasmic, brown) and PSA (cytoplasmic, red) may be reduced or perhaps absent in this sample.
Figure 58:
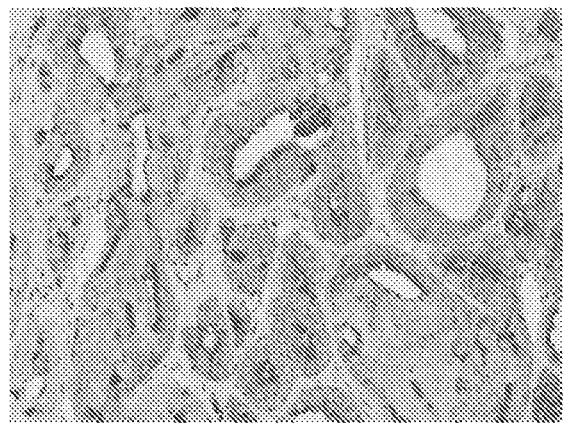
FIG. 58 is a color version of FIG. 23 showing an example of a cocktail of UPII+PAX8+PSA staining prostate cancer. Staining of PSA (red) is cytoplasmic. Staining of UPII (membranous and cytoplasmic, brown) and PAX8 (nuclear, red) may be reduced or perhaps absent in this sample.
Figure 59:
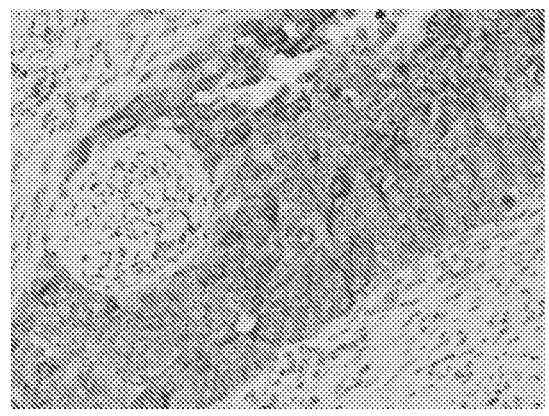
FIG. 59 is a color version of FIG. 24 showing an example of a cocktail of UPII+NKX3.1 staining urothelial carcinoma. Staining of UPII (red) is membranous and cytoplasmic. Staining of NKX3.1 (nuclear, brown) may be reduced or perhaps absent in this sample.
Figure 60:
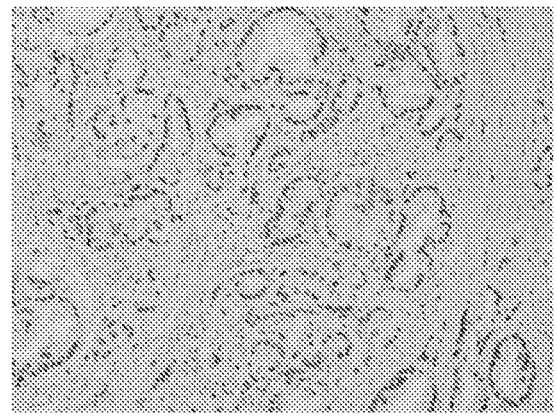
FIG. 60 is a color version of FIG. 25 showing an example of a cocktail of UPII+NKX3.1 staining prostate cancer. Staining of NKX3.1 (brown) is nuclear. Staining of UPII (membranous and cytoplasmic, red) may be reduced or perhaps absent in this sample.
Figure 61:
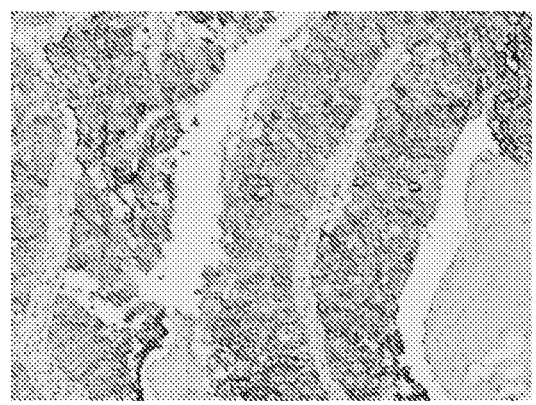
FIG. 61 is a color version of FIG. 26 showing an example of a cocktail of UPII+PAX8+NKX3.1 staining urothelial carcinoma. Staining of UPII (brown) is membranous and cytoplasmic. Staining of PAX8 (nuclear, brown) and NKX3.1 (nuclear, red) may be reduced or perhaps absent in this sample.
Figure 62:
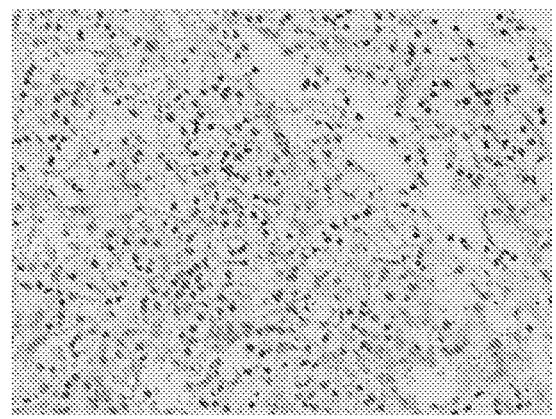
FIG. 62 is a color version of FIG. 27 showing an example of a cocktail of UPII+PAX8+NKX3.1 staining renal cell carcinoma. Staining of PAX8 (brown) is nuclear. Staining of UPII (membranous and cytoplasmic, brown) and NKX3.1 (nuclear, red) may be reduced or perhaps absent in this sample.
Figure 63:
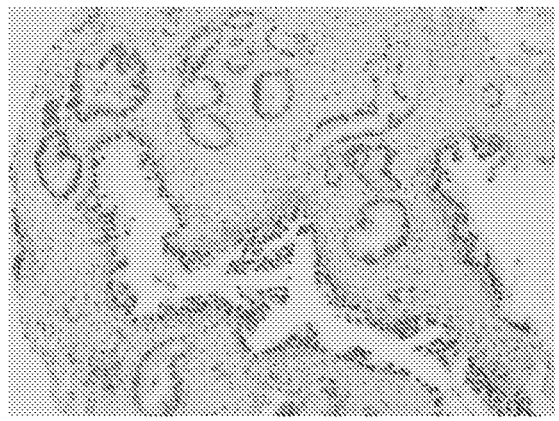
FIG. 63 is a color version of FIG. 28 showing an example of a cocktail of UPII+PAX8+NKX3.1 staining prostate cancer. Staining of NKX3.1 (red) is nuclear. Staining of UPII (membranous and cytoplasmic, brown) and PAX8 (nuclear, brown) may be reduced or perhaps absent in this sample.
Figure 64:
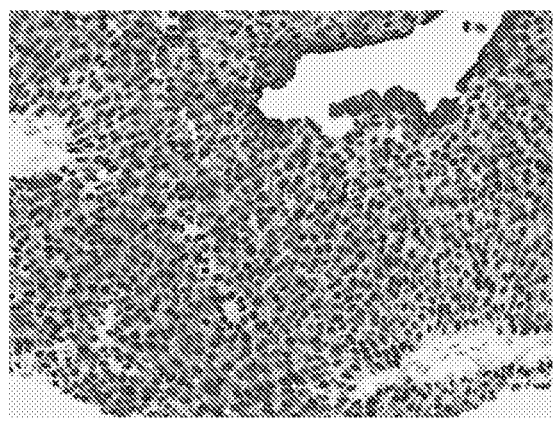
FIG. 64 is a color version of FIG. 29 showing an example of a cocktail of UPII+p63 staining urothelial carcinoma. Staining of p63 (brown) is nuclear. Staining of UPII (red) is membranous and cytoplasmic.
Figure 65:
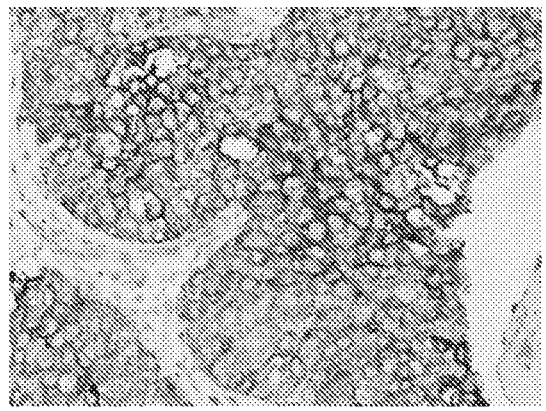
FIG. 65 is a color version of FIG. 30 showing an example of a cocktail of UPII+p63 staining urothelial carcinoma. Staining of UPII (brown) is membranous and cytoplasmic. Staining of p63 (nuclear, brown) may be reduced or perhaps absent in this sample.
Figure 66:
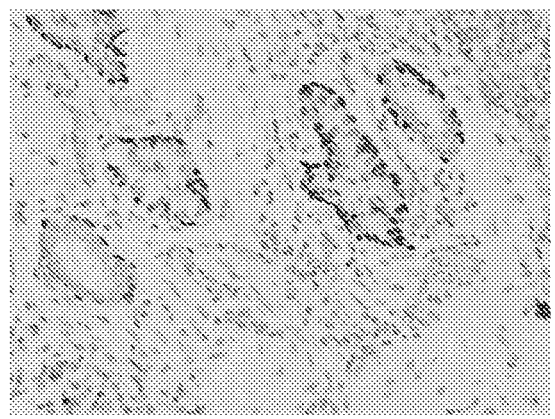
FIG. 66 is a color version of FIG. 31 showing an example of a cocktail of UPII+p63 staining prostatic intraepithelial neoplasia (PIN). Staining of p63 (brown) is nuclear. Staining of UPII (membranous and cytoplasmic, brown) may be reduced or perhaps absent in this sample.
Figure 67:
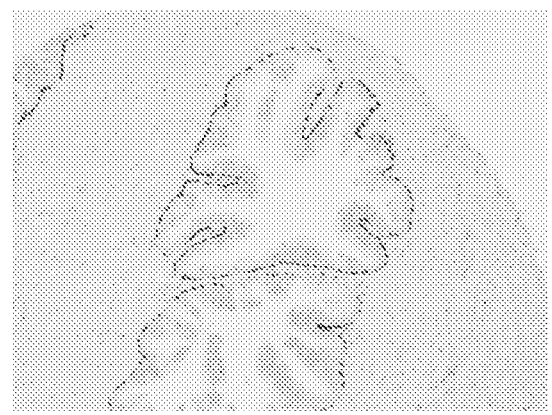
FIG. 67 is a color version of FIG. 32 showing an example of a cocktail of UPII+p63 staining normal prostate. Staining of p63 (brown) is nuclear. Staining of UPII (membranous and cytoplasmic, brown) may be reduced or perhaps absent in this sample.
Figure 68:
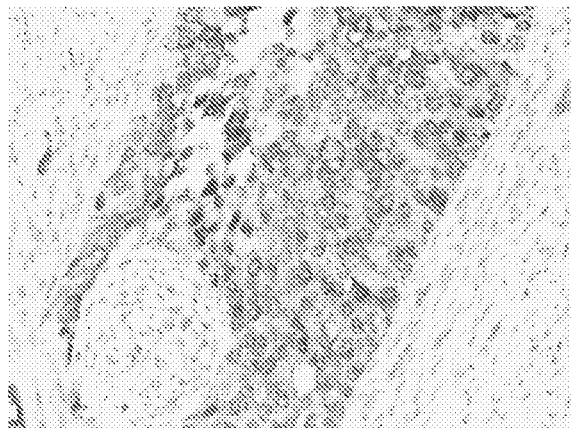
FIG. 68 is a color version of FIG. 33 showing an example of a cocktail of UPII+p40 staining urothelial carcinoma. Staining of p40 (brown) is nuclear. Staining of UPII (red) is membranous and cytoplasmic.

As but one example of an immunoassay method, embodiments of the present invention may provide obtaining tissue from an animal or human to be tested (6), fixing or freezing said tissue (7), treating said fixed or frozen tissue to unmask epitopes to Uroplakin III (8), contacting said treated tissue with an antibody or fragment thereof as discussed herein in an amount and under conditions such that an antibody or fragment thereof binds to a Uroplakin III protein if the protein is present in said tissue (9); and perhaps even detecting the presence of said bound antibodies (10), as schematically represented in FIG. 35.

The present invention may provide, in embodiments, a diagnostic or even prognostic test kit which may include an antibody or fragment thereof (as discussed herein) with an antibody detection element of the antibody or fragment thereof perhaps when bound to an antigen. This may provide a method of contacting a biological sample with an antibody or fragment thereof and even detecting binding of, or even the presence of the antibody or fragment thereof bound to a protein or with an antigen in the biological sample perhaps using an antibody detection element. Embodiments may provide an immunoassay method for detecting Uroplakin II protein in a mammal or human perhaps by obtaining a tissue from an animal or a human to be tested, contacting the tissue with an antibody or fragment thereof in accordance with the various embodiments presented herein perhaps in an amount and under conditions such that the antibody or fragment thereof may bind to a Uroplakin II protein if the protein is present in the tissue; and even detecting the presence of bound antibodies. A biological sample may include but is not limited to blood, urine, urothelial tissue, transitional cell tissue, bladder tissue, normal tissue, neoplastic tissue, kidney tissue, ovarian tissue, thyroid tissue, endometrial tissue, renal tissue, tonsil tissue, pancreas tissue, colon tissue, lymph node tissue, neoplastic pancreatic tissue, stomach tissue, prostate tissue, lung tissue, breast tissue, or the like perhaps depending on the antibody or even cocktail being used.

It is noted that use of terms such as UPII, UPII antibody, UPIII, UPIII antibody, BC21, BC17, or the like may related to anti-UPII antibodies, anti-UPIII antibodies, or the like as appropriate as one skilled in the art would understand.

As can be easily understood from the foregoing, the basic concepts of the present invention may be embodied in a variety of ways. It involves both antibody techniques as well as devices to accomplish the appropriate antibody. In this application, the antibody techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "detection" or "detector" should be understood to encompass disclosure of the act of "detecting"—whether explicitly discussed or not—and, conversely, were there effectively disclosure of the act of "detecting", such a disclosure should be understood to encompass disclosure of a "detector" and even a "means for detecting." Such changes and alternative terms are to be understood to be explicitly included in the description. Further, each such means (whether explicitly so described or not) should be understood as encompassing all elements that can perform the given function, and all descriptions of elements that perform a described function should be understood as a non-limiting example of means for performing that function.

Any law, statutes, regulations, or rules mentioned in this application for patent; or patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed below or in any list of References or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

U.S. Patents

| U.S. Pat No. | Kind Code | Issue Date | Name of Patentee or Applicant of cited Document |
|---|---|---|---|
| 7,846,762 | B2 | 2010 Dec. 7 | Li et al. |

U.S. Patent Application Publications

| Publication Number | Kind Code | Publication Date | Name of Patentee or Applicant of cited Document |
|---|---|---|---|
| 20070015908 | A1 | 2007 Jan. 18 | Fischer et al. |

U.S. Patent Application Publications

| Foreign Document Number | Country Code | Kind Code | Publication Date | Name of Patentee or Applicant of cited Document |
|---|---|---|---|---|
| 2012154983 | WO | A2 | 2012 Nov. 15 | Biocare Medical, LLC |

Non-Patent Literature Documents

Brown, H. M. Et al. Uroplakin-III to Distinguish Primary Vulvar Paget Disease From Paget Disease Secondary to Urothelial Carcinoma, Human Path. 2002; 33:545-548.

Koga, F. et al. Impaired p63 Expression Associates with Poor Prognosis and Uroplakin III Expression in Invasive Urothelial Carcinoma of the Bladder, Clin Cancer Res. 2003; 9:5501-5507.

Logani, S. et al. Immunoprofile of Ovarian Tumors With Putative Transitional Cell (Urothelial) Differentiation Using Novel Urothelial MarkersHistogenetic and Diagnostic Implications, Am J Surg Pathol 2003; 27:1434-1441

Matsumoto, K. et al. Loss Expression of Uroplakin III is Associated with Clinicopathologic Features of Aggressive Bladder Cancer, Urology. 2008; 72:444-449.

Mhawech, P. et al. Immunohistochemical Profile of High-Grade Urothelial Bladder Carcinoma and Prostate Adenocarcinoma, Human Path. 2002; 33:1136-1140.

Ogawa, K. et al. Immunohistochemical Analysis of Uroplakins, Urothelial Specific Proteins, in Ovarian Brenner Tumors, Normal Tissues, and Benign and Neoplastic Lesions of the Female Genital Tract, Am J Pathol. 1999; 155:1047-1050.

Ohtsuka, Y. et al. Loss of uroplakin III expression is associated with a poor prognosis in patients with urothelial carcinoma of the upper urinary tract, BJU International, 2006; 97:1322-1326

Parker, D. C. et. al. Potential Utility of Uroplakin III, Thrombomodulin, High Molecular Weight Cytokeratin, and Cytokeratin 20 in Noninvasive, Invasive, and Metastatic Urothelial (Transitional Cell) Carcinomas, Am J Surg Pathol 2003; 27:1-10.

Wu, X. R. et. al. Mammalian Uroplakins, A group of highly conserved urothelial differentiation-related membrane proteins, J Biol Chem. 1994; 269:13716-13724.

Moll, R. et al. Uroplakins, Specific Membrane Proteins of Urothelial Umbrella Cells, as Histological Markers of Metastatic Transitional Cell Carcinomas, American Journal of Pathology, Vol. 147, No. 5, November 1995.

Kaufmann, O. et al. Uroplakin III Is a Highly Specific and Moderately Sensitive Immunohistochemical Marker for Primary and Metastatic Urothelial Carcinomas, Am J Clin Pathol 2000; 113:683-687

Wu X R, Kong X P, Pellicer A, Kreibich G, Sun T T.; Uroplakins in urothelial biology, function, and disease; Kidney Int. 2009 June; 75(11):1153-65.

Wu X, Kakehi Y, Zeng Y, Taoka R, Tsunemori H, Inui M. J; Uroplakin II as a promising marker for molecular diagnosis of nodal metastases from bladder cancer: comparison with cytokeratin 20.; Urol. 2005 December; 174(6): 2138-42.

Olsburgh J, Harnden P, Weeks R, Smith B, Joyce A, Hall G, Poulsom R, Selby P, Southgate J. J; Uroplakin gene expression in normal human tissues and locally advanced bladder cancer Pathol. 2003 January; 199(1):41-9.

Lu J J, Kakehi Y, Takahashi T, Wu X X, Yuasa T, Yoshiki T, Okada Y, Terachi T, Ogawa O; Detection of circulating cancer cells by reverse transcription-polymerase chain reaction for uroplakin II in peripheral blood of patients with urothelial cancer; Clin Cancer Res. 2000 August; 6(8):3166-71.

Li S M, Zhang Z T, Chan S, McLenan O, Dixon C, Taneja S, Lepor H, Sun T T, Wu X R; Detection of circulating uroplakin-positive cells in patients with transitional cell carcinoma of the bladder; J. Urol. 1999 September; 162(3 Pt 1):931-5.

Kong X T, Deng F M, Hu P, Liang F X, Zhou G, Auerbach A B, Genieser N, Nelson P K, Robbins E S, Shapiro E, Kachar B, Sun T T.; Roles of uroplakins in plaque formation, umbrella cell enlargement, and urinary tract diseases. J Cell Biol. 2004 Dec. 20; 167(6):1195-204.

Okegawa T, Kinjo M, Nutahara K, Higashihara E.; Value of reverse transcription polymerase chain assay in peripheral blood of patients with urothelial cancer. J Urol. 2004 April; 171(4):1461-6.

Hong-Ying Huang, Shahrokh F. Shariat, * Tung-Tien Sun, Herbert Lepor, Ellen Shapiro, Jer-Tsong Hsieh, Raheela Ashfaq, Yair Lotan, and Xue-Ru Wu; Persistent Uroplakin Expression in Advanced Urothelial Carcinomas: Implications in Urothelial Tumor Progression and Clinical Outcome. Hum Pathol. 2007 November; 38(11): 1703-1713.

Hoang, L. L. et al., A Newly Developed Uroplakin II Antibody with Increased Sensitivity in Urothelial Carcinoma of the Bladder, Running Title: Uroplakin II in Urothelial Bladder Carcinoma, submitted for publication to the "Archives of Pathology and Laboratory Medicine" on Apr. 17, 2013

U.S. Nonprovisional application Ser. No. 13/830,473 filed Mar. 14, 2013; entitled Systems and Methods for Anti-Uroplakin III Antibodies U.S. Provisional Application No. 61/706,312 filed Sep. 27, 2012; entitled Systems and Methods for Anti-Uroplakin II Antibodies Budapest restricted certificate of deposit Budapest treaty on the international recognition of the deposit of microorganisms for the purposes of patent procedure international form Receipt in the case of an original deposit issued pursuant to rule 7.3 and viability statement issued pursuant to rule 10.2, Anti-human UPII mouse hybridoma: BC21, PTA-13181, 25 vials, Deposited on Behalf of: Biocare Medical, Inc., Date of Receipt of seeds/strain(s) by the ATCC®: Sep. 6, 2012

Thus, the applicant(s) should be understood to have support to claim and make a statement of invention to at least: i) each of the antibody devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) an apparatus for performing the methods described herein comprising means for performing the steps, xii) the various combinations and permutations of each of the elements disclosed, xiii) each potentially dependent claim or concept as a dependency on each and every one of the independent claims or concepts presented, and xiv) all inventions described herein.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in *Hakim v. Cannon Avent Group*, PLC, 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible. The use of the phrase, "or any other claim" is used to provide support for any claim to be dependent on any other claim, such as another dependent claim, another independent claim, a previously listed claim, a subsequently listed claim, and the like. As one clarifying example, if a claim were dependent "on claim 20 or any other claim" or the like, it could be re-drafted as dependent on claim 1, claim 15, or even claim 25 (if such were to exist) if desired and still fall with the disclosure. It should be understood that this phrase also provides support for any combination of elements in the claims and even incorporates any desired proper antecedent basis for certain claim combinations such as with combinations of method, apparatus, process, and the like claims.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. An isolated antibody produced by the hybridoma deposited with the American Type Culture Collection (ATCC) under ATCC Patent Deposit Designation No. PTA-13181 or an isolated antigen binding fragment of the isolated antibody, wherein the antibody or antigen binding fragment thereof specifically binds Uroplakin II comprising SEQ ID NO: 4.

2. A hybridoma cell that is deposited at the American Type Culture Collection (ATCC) under ATCC Patent Deposit Designation No. PTA-13181.

3. The hybridoma cell according to claim 2 further comprising an antibody or antigen binding fragment thereof produced by said hybridoma cell.

4. A method for producing a monoclonal antibody according to claim 1 comprising the steps of:
culturing said hybridoma deposited with the American Type Culture Collection (ATCC) under ATCC Patent Deposit Designation No. PTA-13181 which produces a monoclonal antibody capable of specifically recognizing Uroplakin II; and
allowing said hybridoma to produce the monoclonal antibody.

5. A composition comprising the isolated antibody or isolated antigen binding fragment thereof of claim 1 and at least one additional isolated antibody or isolated antigen binding fragment thereof, wherein the at least one additional isolated antibody or isolated antigen binding fragment thereof specifically binds to an antigen selected from the group consisting of GATA-3, p63, Uroplakin III, PAX8, NKX3.1, PSA and p40.

6. The composition according to claim 5 wherein said isolated antibody or isolated antigen binding fragment thereof and said at least one additional isolated antibody or isolated antigen binding fragment thereof each bind specifically to proteins selected from a group consisting of:
Uroplakin II and GATA-3;
Uroplakin II and p63;
Uroplakin II and Uroplakin III;
Uroplakin II and PAX8;
Uroplakin II and NKX3.1;
Uroplakin II and PSA;
Uroplakin II and Uroplakin III and GATA-3;
Uroplakin II and PAX8 and PSA;
Uroplakin II and PAX8 and NKX3.1; and
Uroplakin II and p40.

7. The isolated antibody or isolated antigen binding fragment thereof of claim 1, wherein the isolated antibody or isolated antigen is conjugated with a label.

8. An antibody according to claim 7 wherein said label is selected from a group consisting of a radioactive element, magnetic particles, radioisotope, fluorescent dye, enzyme, toxin, signal, stain, detection enzymes, horseradish peroxidase (HRP), alkaline phosphatase (AP), beta-galactosidase, chromogens, Fast Red, 3,3'-diaminobenzidine, 3-amino-9-ethylcarbazole, 5-bromo-4-chloro-3-indolyl phosphate, 3,3', 5,5'-tetramethylbenzidine, 5-bromo-4-chloro-3-indolyl-β-D-glucuronide, and any combination thereof.

9. A kit comprising:
the isolated antibody or isolated antigen binding fragment thereof of claim 1; and
an antibody detection reagent of said isolated antibody or isolated antigen binding fragment thereof of claim 1, when bound the Uroplakin II antigen.

10. A method for detecting Uroplakin II in a biological sample comprising the steps of:
(a) providing the kit of claim 9; and
(b) detecting binding of said isolated antibody or said isolated antigen binding fragment thereof with the Uroplakin II antigen with an immunoassay comprising:
(i) contacting the biological sample with the isolated antibody or isolated antigen binding fragment thereof produced by hybridoma deposited with the American Type Culture Collection (ATCC) under ATCC Patent Deposit Designation No. PTA-13181, wherein the antibody or antigen fragment thereof specifically binds Uroplakin II comprising SEQ ID NO: 4 to form a complex; and
(ii) detecting the complex with the antibody detecting reagent provided in the kit, wherein the immunoassay is selected from the group consisting of immunohistochemistry (IHC), IHC of FFPE, IHC of frozen-tissue sections, immunocytochemistry, and ELISA.

11. The method according to claim 10 wherein said biological sample comprises blood, urine, urothelial tissue, transitional cell tissue, and bladder tissue.

12. The method according to claim 10 wherein said biological sample is selected from a group consisting of a normal tissue, neoplastic tissue, bladder tissue, kidney tissue, ovarian tissue, thyroid tissue, endometrial tissue, renal tissue, tonsil tissue, pancreas tissue, colon tissue, lymph node tissue, stomach tissue, prostate tissue, lung tissue and breast tissue.

* * * * *